United States Patent
Zhou et al.

(10) Patent No.: US 7,241,266 B2
(45) Date of Patent: *Jul. 10, 2007

(54) TRANSDUCER FOR EMBEDDED BIO-SENSOR USING BODY ENERGY AS A POWER SOURCE

(75) Inventors: Peter Zhou, Riverside, CA (US); Dexing Pang, Riverside, CA (US); William Li, Riverside, CA (US)

(73) Assignee: Digital Angel Corporation, Del Ray Beach, FL (US)

( * ) Notice: Subject to any disclaimer, the term of this patent is extended or adjusted under 35 U.S.C. 154(b) by 360 days.

This patent is subject to a terminal disclaimer.

(21) Appl. No.: 10/850,315

(22) Filed: May 20, 2004

(65) Prior Publication Data

US 2005/0261563 A1     Nov. 24, 2005

(51) Int. Cl.
*A61B 5/00* (2006.01)
*A61B 5/05* (2006.01)

(52) U.S. Cl. ..................... 600/365; 600/347
(58) Field of Classification Search ............. None
See application file for complete search history.

(56) References Cited

U.S. PATENT DOCUMENTS

| | | | |
|---|---|---|---|
| 5,914,026 A | 6/1999 | Blubaugh, Jr. et al. | |
| 6,295,466 B1 * | 9/2001 | Ishikawa et al. | 600/509 |
| 6,336,794 B1 * | 1/2002 | Kim | 417/363 |
| 6,366,794 B1 * | 4/2002 | Moussy et al. | 600/345 |
| 6,546,268 B1 * | 4/2003 | Ishikawa et al. | 600/345 |
| 6,559,620 B2 * | 5/2003 | Zhou et al. | 320/101 |
| 6,659,948 B2 * | 12/2003 | Lebel et al. | 600/300 |
| 2001/0035723 A1 * | 11/2001 | Pelrine et al. | 318/116 |

* cited by examiner

Primary Examiner—Robert L. Nasser, Jr.
(74) Attorney, Agent, or Firm—Stroock & Stroock & Lavan LLP

(57) ABSTRACT

Provided is a bio-sensor system which utilizes radio frequency identification technology and which includes a remote transponder in wireless communication with an implantable on-chip transponder. A power supply collects alternating current voltage pulses from an electro-active polymer generator embedded in muscle tissue for generating power for the on-chip transponder. The power supply is specifically adapted to provide a stable and precise sensor reference voltage to a sensor assembly to enhance the accuracy of measurements of a physiological parameter of a patient. The remote transponder receives data representative of the physiological parameter such as glucose concentration levels. The data is processed and transmitted to the remote transponder by the on-chip transponder. The precision and stability of the sensor reference voltage is enhanced by the specific circuit architecture of a glucose sensor to allow for relatively accurate measurement of glucose concentration levels without the use of a microprocessor.

20 Claims, 11 Drawing Sheets

TRANSDUCER FOR EMBEDDED BIO-SENSOR USING BODY ENERGY AS A POWER SOURCE

CROSS-REFERENCE TO RELATED APPLICATIONS

Not Applicable

STATEMENT RE: FEDERALLY SPONSORED RESEARCH/DEVELOPMENT

Not Applicable

BACKGROUND OF THE INVENTION

The present invention relates to sensor devices and, more particularly, to an implantable bio-sensor system that includes an electro-active polymer (EAP) generator which is specifically adapted to provide substantially continuous and reliable power to the bio-sensor system as a result of mechanical flexing of the EAP generator in response to movement of muscle within which the EAP generator may be embedded.

Blood glucose concentration level of a patient is normally controlled by the pancreas. However, for patients suffering from diabetes, the pancreas does not properly regulate the production of insulin as needed to metabolize food into energy for the individual. For diabetic patients, glucose levels must be checked or monitored several times throughout the day so that insulin may be periodically administered in order to maintain the glucose concentration at a normal level. In one popular method, the glucose level is monitored by first obtaining a sample of blood from finger-pricking.

The glucose level of the blood sample is then placed on a glucose measurement strip and a subsequent chemical reaction produces a color change that may be compared to a reference chart. In this manner, the reaction of the blood sample with the glucose measurement strip provides an indication as to whether the glucose level is abnormally low or high such that the diabetic patient may administer the proper amount of insulin in order to maintain the glucose concentration within a predetermined range. Such administration of insulin is typically performed by way of self-injection with a syringe.

Unfortunately, the finger-pricking method of glucose testing is uncomfortable as both the blood-pricking and the insulin injections are painful and time-consuming such that many diabetic patients are reluctant to check their glucose levels at regular intervals throughout the day. Unfortunately, glucose levels often fluctuate throughout the day. Therefore, even diabetic patients who are otherwise consistent in checking their glucose levels at regular intervals throughout the day may be unaware of periods wherein their glucose levels are dangerously low or high. Furthermore, the finger-pricking method is dependent on patient skill for accurate testing such that the patient may rely on erroneous data in determining the dosage level of insulin. Finally, self-monitoring of glucose levels imposes a significant burden on less capable individuals such as the young, the elderly and the mentally-challenged.

At the time of this writing, it is estimated that 17 million people in the United States, or about six percent of the population, have diabetes. Due in part to dietary habits and an increasingly sedentary lifestyle, particularly among children, diabetes is expected to increase at the rate of about 7 percent every year such that the disease is predicted to eventually reach epidemic proportions. In addition, the current cost of diabetes in the United States alone is estimated at over $120 billion with the total U.S. sales of the glucose measuring strips alone estimated at about $2 billion. Thus, there is a demand for continuous, reliable and low-cost monitoring of glucose levels of diabetic patients due to the increasing number of people diagnosed with diabetes.

Included in the prior art are several implantable devices that have been developed in an effort to provide a system for continuous glucose monitoring. In some of the prior art implantable devices, an electrochemical sensor may be used to measure glucose concentration levels. Such sensors may use an amperometric detection technique wherein oxidation or reduction of a compound is measured at a working electrode in order to determine substance concentration levels. A potentiostat is used to apply a constant potential or excitation voltage to the working electrode with respect to a reference electrode.

When measuring glucose concentration levels in the blood, glucose oxidase (GOX) is typically used as a catalyst. Upon applicaiton of the excitation voltage to the working electrode, the GOX oxidize glucose in the patient's blood and forms gluconic acid, leaving behind two electrons and two protons and reducing the GOX. Oxygen that is dissolved in the patient's blood then reacts with GOX by accepting the two electrons and two protons to form hydrogen peroxide ($H_2O_2$) and regenerating oxidized GOX. The cycle repeats as the regenerated GOX reacts once again with glucose.

The consumption of $O_2$ or the formation of $H_2O_2$ is subsequently measured at the working electrode which is typically a platinum electrode. As oxidation occurs at the working electrode, reduction also occurs at the reference electrode which is typically a silver/silver chloride electrode. The more oxygen that is consumed, the greater the amount of glucose in the patient's blood. In the same reaction, the rate at which $H_2O_2$ is produced is also indicative of the glucose concentration level in the patient's blood. In this manner, the electrochemical sensor measures the glucose concentration level.

Unfortunately, such implantable devices of the prior art suffer from several deficiencies that detract from their overall utility. One such deficiency is that implantable devices may expend a substantial amount of power in sensing and processing sensor signals. The power requirement for such devices necessitates the use of large batteries in order to prolong the useful life. Implantable devices having large batteries as the power source may require periodic surgeries for replacement of the batteries when the capacity drops below a minimum level. Furthermore, large batteries may contain large amount of hazardous chemicals or substances that may present a risk of harm to the patient due to toxicity of such substances which may leak into the patient after implantation.

Also, due to the relatively limited power capacity of batteries, the range of functions that may be performed by the implantable device may be somewhat limited. For example, it may be desirable to monitor multiple physiological parameters in addition to glucose concentration levels of the patient. In such cases, the implantable device may include multiple sensors wherein each sensor simultaneously monitors a different physiological parameter of the patient. For example, in addition to monitoring glucose concentration levels, the temperature and heart rate of the patient may also be monitored. Unfortunately, a device having multiple sensors may consume more power than can be supplied by a battery that is miniaturized to a size that is small enough for use in an implantable device.

As can be seen, there is a need for an implantable bio-sensor system that overcomes the above-described deficiencies associated with powering the bio-sensor system. More specifically, there exists a need in the art for an implantable bio-sensor system that is not solely dependent upon batteries for power. There also exists a need in the art for an implantable bio-sensor system that provides an essentially unlimited or continuous power supply such that multiple sensors may allow for simultaneous and selective monitoring of multiple physiological parameters of the patient.

BRIEF SUMMARY OF THE INVENTION

Provided is a uniquely configured telemetric bio-sensor system which is powered by an electro-active polymer (EAP) generator. The bio-sensor system utilizes radio frequency identification (RFID) technology and includes a remote transponder that is in wireless communication with an on-chip transponder that is implantable within a host such as a human patient. The on-chip transponder includes a power supply connected to the EAP generator which is specifically adapted to generate a power signal for powering the major components of the on-chip transponder.

In addition, the power supply is configured to provide a substantially stable and precise voltage to a sensor assembly of the on-chip transponder. The sensor assembly measures data such as a physiological parameter of the patient when requested by the remote transponder. The data may include identification data regarding, for example, the patient's age and medical history. The data is then processed by the on-chip transponder which then transmits the data back to the remote transponder for storing or readout of the data.

The EAP generator is preferably embedded in muscle tissue of the patient and is configured to generate the power signal as result of mechanical flexing of the EAP generator in response to muscle movement such as the rhythmic muscle movement that occurs during breathing. In the case of breathing muscles, such rhythmic movement causes the EAP generator to undergo a flex-and-return cycle at a substantially continuous rate of about once every six seconds, depending on the breathing rate of the patient. Such substantially continuous power as provided by the EAP generator enables a more robust radio link between the remote transponder and the on-chip transponder because transmission power and data message length are not dependent on battery size.

Advantageously, the power supply of the on-chip transponder provides substantially stable and accurate power to the sensor assembly in order to increase the accuracy with which physiological parameters of the patient are measured. The technique of generating the stable and precise voltage may be applied to a 2-pin glucose sensor as well as to a 3-pin glucose sensor for relatively accurate measurement of the patient's glucose concentration level. Importantly, the bio-sensor system provides the stable and precise voltage to the sensor assembly without the use of a microprocessor such that cost and power consumption of the on-chip transponder may be reduced.

The bio-sensor system may be configured to operate in duplex mode wherein the on-chip transponder additionally includes an intelligent radio frequency (RF) receiver to enable features such as selection between multiple sensors and/or continuous readout of data (e.g., physiological parameters of the patient). For example, the sensor may be configured as at least one of the following: a pressure transducer, a blood sugar sensor, a blood oxygen sensor, a heart rate monitor, a respiratory rate sensor, etc.

BRIEF DESCRIPTION OF THE DRAWINGS

These as well as other features of the present invention will become more apparent upon reference to the drawings wherein.

DETAILED DESCRIPTION OF THE INVENTION

Figure 1A:
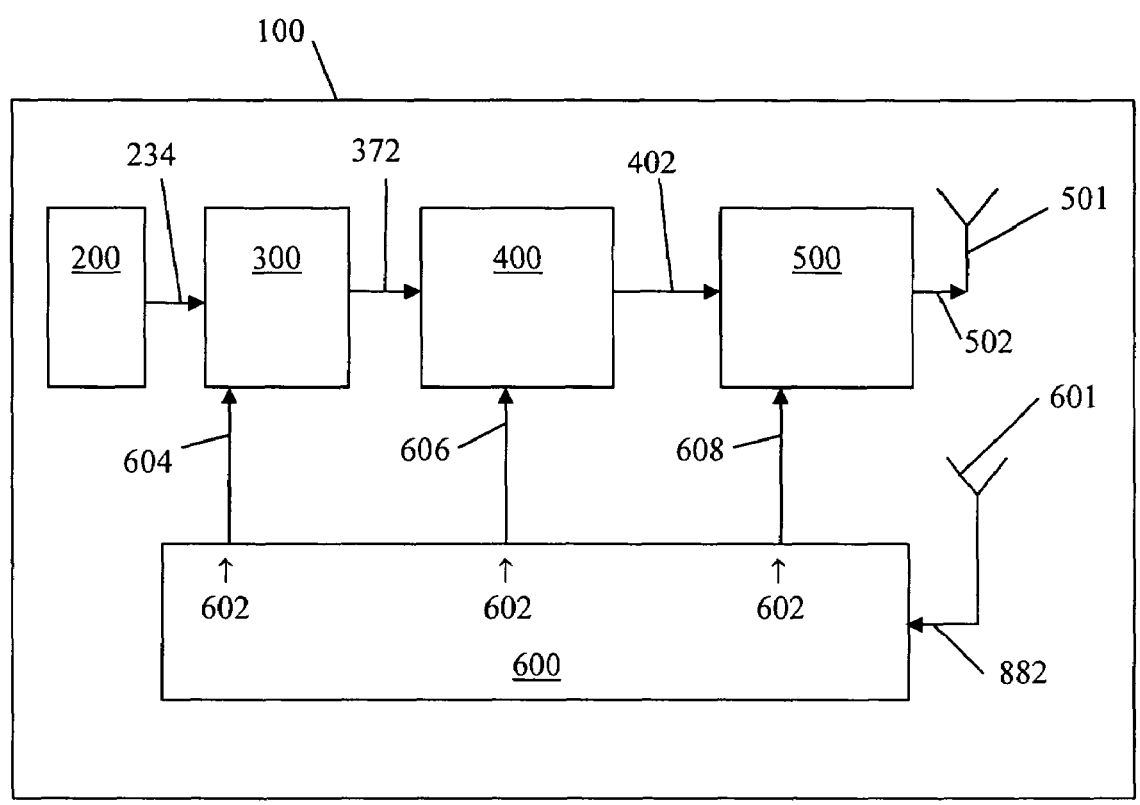
FIG. 1a is a block diagram of a sensor assembly and an on-chip transponder of an implantable bio-sensor system of the present invention in an embodiment enabling simplex operation wherein the content and duration of a signal transmitted by the on-chip transponder is pre-programmed.

Referring now to the drawings wherein the showings are for purposes of illustrating various aspects of the invention and not for purposes of limiting the same, provided is a uniquely configured telemetric bio-sensor system 10 which is powered by an electro-active polymer (EAP) generator 610. The bio-sensor system 10 utilizes radio frequency identification (RFID) technology and includes a remote transponder 800 that is in wireless communication with the EAP generator-powered on-chip transponder 100. A power supply 600 is included with the on-chip transponder 100. The power supply 600 includes the EAP generator 610 which is specifically adapted to generate a power signal 602 for powering the major components of the on-chip transponder 100 as well as provide a substantially stable and precise voltage to a sensor assembly 200 of the on-chip transponder 100. The on-chip transponder 100 is implantable into a host such as a human patient.

The EAP generator 610 is preferably embedded in muscle tissue of the patient and is configured to generate a power signal 602 as a result of mechanical flexing of the EAP generator 610 in response to muscle movement such as the rhythmic muscle movement that occurs during breathing. Advantageously, such rhythmic muscle movement causes the EAP generator 610 to undergo a flex-and-return cycle at a substantially continuous rate of about once every six seconds, depending on the breathing rate of the patient. Such substantially continuous power as provided by the EAP generator 610 enables a more robust radio link between the remote transponder 800 and the on-chip transponder 100 because transmission power and data message length are not dependent on battery size.

The remote transponder 800, which may be a compact handheld device, may be manually placed within a predetermined distance (e.g., within several feet) of the on-chip transponder 100 in order to request telemetry data from the on-chip transponder 100. The remote transponder 800 may alternatively be fixedly mounted and may be configured to automatically transmit telemetry request data to the patient and, hence, the on-chip transponder 100 when the patient moves within the predetermined distance to the remote transponder 800. Regardless of whether it is handheld, fixedly mounted or otherwise supported, the remote transponder 800 is configured to remotely receive data representative of a physiological parameter of the patient as well as identification data such that the data may be stored or displayed.

Importantly, the application of the substantially stable voltage to the sensor assembly 200 allows for relatively accurate measurement of the physiological parameter of the patient such as measurement of a glucose concentration level by a glucose sensor 210. As will be demonstrated below, the technique of generating the stable and precise voltage may be applied to a 2-pin glucose sensor 210 as well as to a 3-pin glucose sensor 210. Importantly, the bio-sensor system 10 provides the stable and precise voltage to the sensor assembly 200 without the use of a microprocessor such that cost and power consumption of the on-chip transponder 100 may be reduced.

In its broadest sense, the bio-sensor system 10 and operational method of use thereof comprises the implantable on-chip transponder 100 and the remote transponder 800 in wireless communication with one another. As mentioned above, the sensor assembly 200 is connected to or integral with the on-chip transponder 100 and may be implanted in the patient with the on-chip transponder 100. The EAP generator 610 may be embedded in muscle tissue of the patient and may be electrically connected to the on-chip transponder 100 using conventional conductive wires or any other suitable means. The bio-sensor system 10 is configured such that the remote transponder 800 may enable readout of one or more of the physiological parameters that are measured, processed and transmitted by the on-chip transponder 100 upon request by the remote transponder 800. The bio-sensor system 10 may be configured to operate in simplex mode as shown in FIG. 1*a*.

Figure 1B:
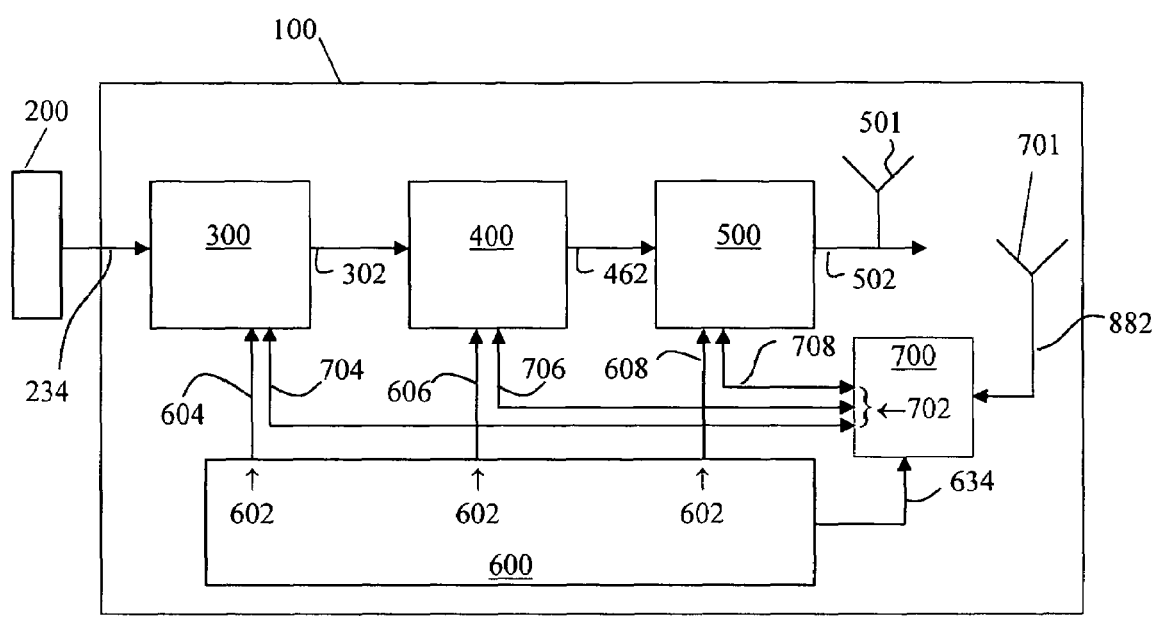
FIG. 1b is a block diagram of the sensor assembly and the on-chip transponder of the bio-sensor system in an embodiment enabling duplex operation wherein the duration and content of signals transmitted by the on-chip transponder to a remote transponder, and vice versa, is selectable.

Alternatively, the bio-sensor system 10 may be configured to operate in duplex mode as shown in FIG. 1*b* wherein the on-chip transponder 100 additionally includes an intelligent radio frequency (RF) receiver. When provided with the RF receiver 700, the bio-sensor system 10 enables features such as selection between multiple sensors 210 and/or continuous readout of data (e.g., physiological parameters of the patient) in addition to readout of identification data which may be correlated to a patient database containing information regarding the patient's identity as well as information regarding the patient's age, weight, medical history, etc.

Referring more particularly now to FIGS. 1*a* and 1*b*, shown are block diagrams of the sensor assembly 200 as connected to the on-chip transponder 100 of the bio-sensor system 10 for respective embodiments enabling simplex and duplex operation. The on-chip transponder 100 includes the sensor assembly 200 having the sensor 210. The sensor 210 may be configured as the 2-pin glucose sensor 210 or as 3-pin glucose sensor 210 as was mentioned above. However, any other sensor may be used with the on-chip transponder 100. For example, the sensor 210 may be configured as at least one of the following: a pressure transducer, a blood sugar sensor, a blood oxygen sensor, a heart rate monitor, a respiratory rate sensor, etc. In this regard, the sensor 210 may be configured as any type of sensor for measuring, monitoring or detecting any type of physiological parameter of the patient.

Figure 2:
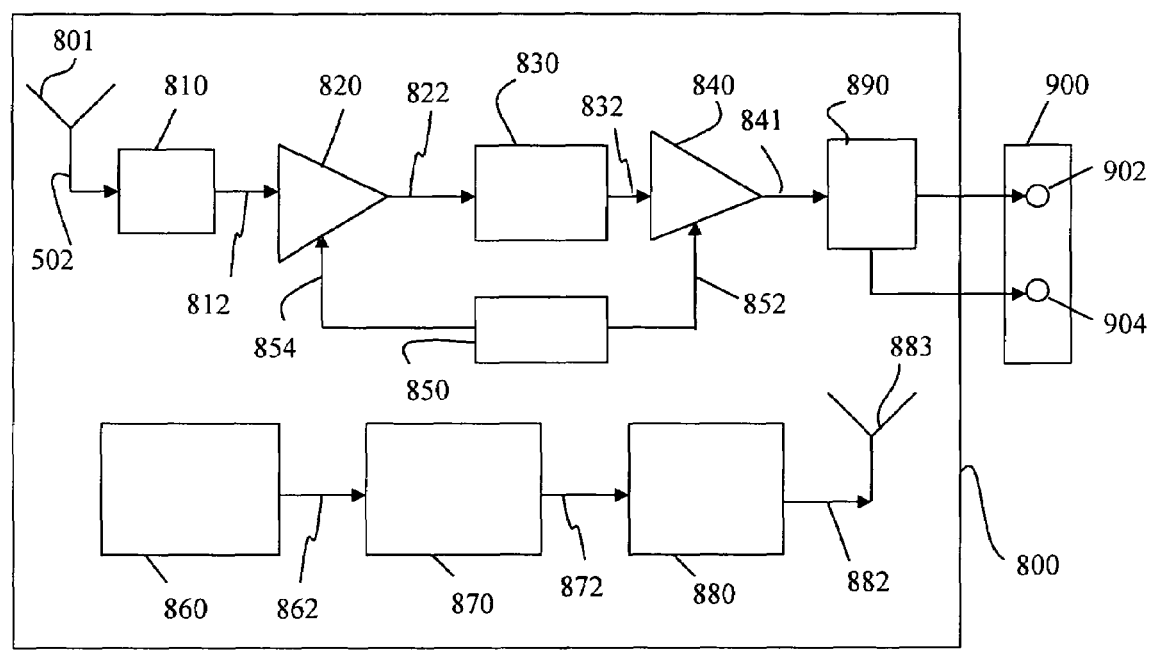
FIG. 2 is a block diagram of a remote transponder of the implantable bio-sensor system.

Shown in FIG. 2 is a block diagram of the remote transponder 800. The remote transponder 800 is configured to wirelessly request data regarding the physiological parameter by transmitting a scanner signal 882 to the on-chip transponder 100. The remote transponder 800 is also configured to receive a data signal 462 representative of the physiological parameter from the on-chip transponder 100. In the same manner, the on-chip transponder 100 is configured to communicate with the remote transponder 800 and receive the scanner signal 882 and transmit the data signal 462 therefrom once the remote transponder 800 and on-chip transponder 100 are within sufficiently close proximity to one another to enable wireless communication therebetween.

Components of the on-chip transponder 100 for the embodiment of the bio-sensor system 10 enabling simplex operation include: the sensor 210, the power supply 600, an analog-to-digital (A/D) assembly 300, a data processor 400 and an RF transmitter 500, as shown in FIG. 1*a*. For embodiments of the bio-sensor system 10 enabling duplex operation, the RF receiver 700 is included with the on-chip transponder 100, as shown in FIG. 1*b*. Each of the components of the on-chip transponder 100 may also be electrically interconnected via conventional conductive wiring. However, electrical connections may preferably be provided using conventional integrated circuit technology such that the on-chip transponder 100 may be packaged into a sufficiently small size for implantation into the patient.

The sensor 210 is configured to generate a sensor signal 234 representative of the physiological parameter of the patient and is made up of a positive signal and a negative signal transmitted in parallel and sent from the sensor 210 to the A/D assembly 300, as shown in FIGS. 1*a* and 1*b*. For the embodiment of the bio-sensor system 10 enabling simplex operation, the power supply 600 receives the scanner signal 882 at antenna 601. The scanner signal 882 is representative of a telemetry request for data. The telemetry request is transmitted to major components of the on-chip transponder 100 such that physiological parameters may be measured, processed and transmitted back to the remote transponder 800

For the embodiment of the bio-sensor system 10 enabling duplexing, the RF receiver 700 receives the scanner signal 882 at antenna 701. For both embodiments of the bio-sensor system 10 (i.e., the simplex embodiment and the duplex embodiment), the power supply 600 is configured to generate the power signal 602 for powering the on-chip transponder 100, including the RF receiver 700. The A/D assembly 300 is connected to the power supply 600 via power line 604 to receive the power signal 602. The A/D assembly 300 is also connected to the sensor 210 to receive the analog sensor signal 234 therefrom. Once powered by the power signal 602, the A/D assembly 300 is configured to generate a digital signal 372 in response to the analog sensor signal 234 coming from the sensor 210.

Referring still to FIGS. 1a and 1b, the data processor 400 is connected to the A/D assembly 300 and the power supply 600 and is configured to receive the power signal 602, via power line 606, as well as the digital signal 372 from the A/D assembly 300. Upon powering by the power signal 602, the data processor 400 is configured to generate a data signal 462 in response to the digital signal 372. In general, the data processor 400 receives the digital signal 372 and filters, amplifies and/or encodes the digital signal 372 to generate the data signal 462. The data processor 400 may be configured to gate the data signal 462 to determine when to transmit the data signal 462 to the remote transponder 800. In addition, the data processor 400 may also be configured to sum the data signal 462 with other data (i.e., from other sensors 210), as will be explained in greater detail below.

The RF transmitter 500 is connected to the power supply 600 via power line 608 to receive the power signal 602. The RF transmitter 500 is also connected to the data processor 400 and is configured to receive the data signal 462 therefrom. The RF transmitter 500 is also configured to modulate, amplify, filter and transmit the data signal 462 back to the remote transponder 800. In general, the RF transmitter 500 impresses (i.e., modulates) the data signal 462 onto a radio carrier of a desired frequency, amplifies the modulated signal and sends the modulated signal to antenna 501 for radiation to the remote transponder 800.

The power supply 600 circuitry is configured similar to the circuitry of a voltage regulator wherein reference diodes and resistors are arranged in such a manner as to generate an approximate supply voltage, as is well known in the art. However, the power supply 600 is also specifically configured to supply a suitable voltage to the sensor 210 processing circuitry without delivering substantial current so as to reduce complexity. Thus, in addition to collecting, rectifying and regulating power for supply to the A/D assembly 300, data processor 400 and RF transmitter 500, the power supply 600 also provides the substantially stable and precise voltage to the sensor assembly 200.

Figure 8A:
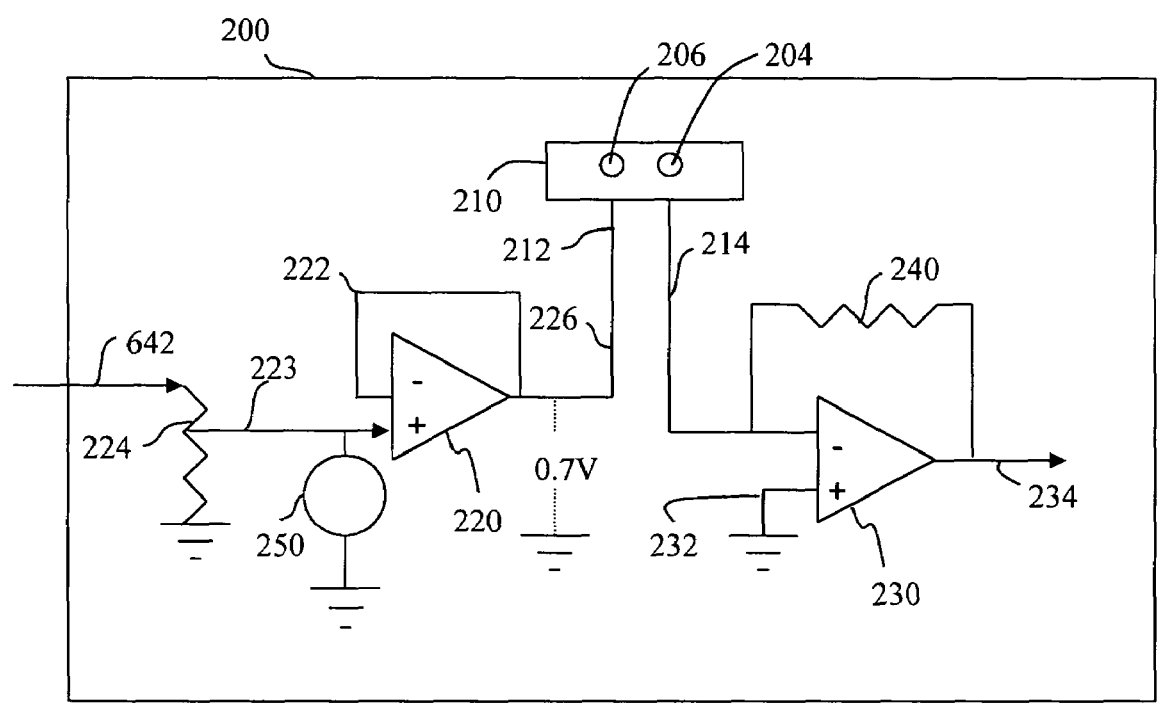
FIG. 8a is a schematic representation of a 2-pin glucose sensor as may be incorporated into the sensor assembly.
Figure 8B:
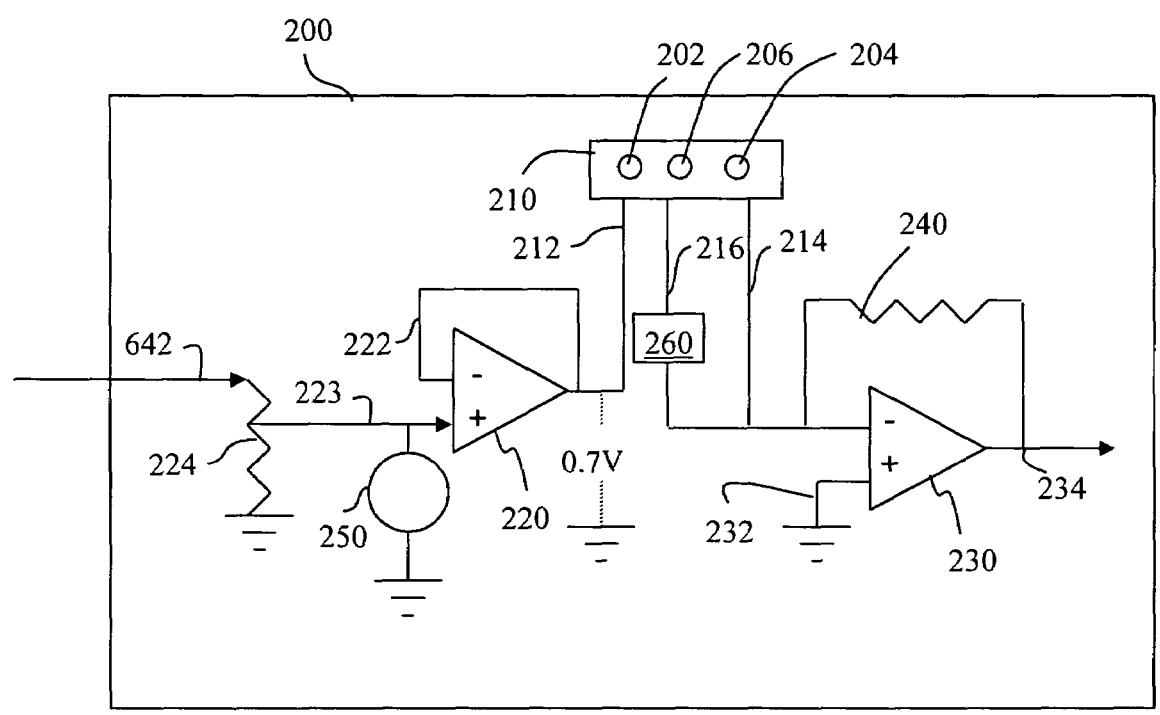
FIG. 8b is a schematic representation of a 3-pin glucose sensor as may be incorporated into the sensor assembly.

More specifically, the power supply 600 is configured to supply a substantially non-deviating sensor reference voltage signal 642 to the sensor 210 in order to enhance the accuracy with which the physiological parameter is measured. The precision and stability of the sensor reference voltage signal 642 (i.e., the sensor 210 power) is enhanced by the specific circuit architecture of the glucose sensor 210, as is shown in FIGS. 8a and 8b and as will be described in greater detail below. In this manner, the accuracy of glucose concentration levels, as represented by an output signal from the glucose sensor 210, is improved. As was earlier mentioned, once the physiological parameter is measured by the sensor 210, the remote transponder 800 is configured to receive the data signal 462 from the RF transmitter 500 and extract data representative of the physiological parameter for storage and/or display.

For embodiments of the bio-sensor system 10 enabling duplex operation, the on-chip transponder 100 additionally includes the RF receiver 700 which is configured to receive the scanner signal 882 from the remote transponder 800, as shown in FIG. 1b. In a broadest sense, the scanner signal 882 is received at antenna 701 and is decoded by the RF receiver 700 to inform the on-chip transponder 100, via a message signal 702, that a request for data has been made. The power supply 600 generates the power signal 602 for relay to the A/D assembly 300, the data processor 400 and the RF transmitter 500 via respective ones of the power lines 604, 606, 608, as will be described in greater detail below.

The RF receiver 700 is configured to filter, amplify and demodulate the scanner signal 882 and generate the message signal 702 for delivery to controlling components of the on-chip transponder 100. More specifically, the message signal 702 is transmitted to the A/D assembly 300, the data processor 400 and the RF transmitter 500 via respective ones of the message/control lines 704, 706, 708, as shown in FIG. 1b. The RF receiver 700 may be in two-way communication with the A/D assembly 300, the data processor 400 and the RF transmitter 500 via respective ones of the message/control lines 704, 706, 708 through which the message signal 702 may be transmitted.

For configurations of the bio-sensor system 10 having a plurality of sensors 210, each one of the sensors 210 may be operative to sense a distinct physiological parameter of the patient and generate the sensor signal 234 representative thereof. For example, an additional one of the sensors 210 may be provided to measure an internal body temperature of the patient. Still further, an additional one of the sensors 210 may be provided to measure a blood pressure level of the patient. The plurality of sensors 210 may generate a plurality of sensor signals 234. The RF receiver 700 may be configured to coordinate requests for data from one or more of the plurality of sensors 210 for subsequent transmission of the data back to the remote transponder 800, as will be described in greater detail below. For embodiments of the bio-sensor system 10 having multiple sensors 210, the data processor 400 may be configured to assign a preset identification code to the digital signal 372 for identifying the sensor 210 from which the sensor signal 234 originates. In such an embodiment, the A/D assembly 300 may include a switch 310 that is responsive to the message signal 702 and which is operative to select among the plurality of sensor signals 234 for subsequent transmission thereof.

Referring now to FIGS. 8a and 8b, for configurations of the bio-sensor system 10 wherein the sensor 210 is a glucose sensor 210 having an electrode assembly 201, the specific circuit architecture of the glucose sensor 210 is preferably such that the sensor reference voltage signal 642 is supplied to the electrode assembly 201 at a substantially constant value of about positive 0.7 volts. Advantageously, the stability and accuracy of the sensor reference voltage signal 642 is achieved without the use of a microprocessor. The circuit architecture includes an electrode assembly 201 having a first terminal 202 (i.e., a working electrode) and a second terminal 204 (i.e., a reference electrode) that are both placed in fluid communication with the patient's blood.

The 2-pin glucose sensor 210 may be configured to measure the glucose level using glucose oxidase (GOX) as a catalyst to cause oxidation of glucose in the patient's blood which forms gluconic acid and which reduces the GOX. Oxygen ($O_2$) in the patient's blood reacts with the GOX to form hydrogen peroxide ($H_2O_2$) and regenerate the oxidized GOX. The consumption of $O_2$ or the formation of $H_2O_2$ is measured at the first terminal 202, which may be fabricated of platinum. While oxidation occurs at the first terminal 202, reduction is measured at the second terminal 204, which may be fabricated of silver/silver chloride. The rate at which $O_2$ is consumed and $H_2O_2$ is formed is indicative of the glucose concentration level in the patient's blood. Advantageously, supplying the sensor reference voltage signal 642 to the first terminal 202 at a substantially constant value of about positive 0.7 increases the accuracy with which the glucose concentration level may be measured by the 2-pin glucose sensor 210 as well as the 3-pin glucose sensor 210.

Referring still to FIG. 8a, measurement accuracy of glucose concentration level by the 2-pin glucose sensor 210 is enhanced by the circuit architecture thereof. As can be seen, the 2-pin glucose sensor 210 includes a first precision resistor 224, a first operational amplifier 220, a voltmeter 250, a second operational amplifier 230 and a tunable second precision resistor 240. The first precision resistor 224 is connected to the power supply 600 and is configured to receive the sensor reference voltage signal 642 therefrom for excitation of the glucose sensor 210. The first operational amplifier 220 is connected to the first precision resistor 224 through the first signal line 212 and is configured to receive the sensor reference voltage signal 642. The first operational amplifier 220 discharges a precision sensor reference voltage signal 223 at a non-inverting input 232 thereof in response to the sensor reference voltage signal 642.

The voltmeter 250 is connected to a non-inverting input of the first operational amplifier 220 and the first precision resistor 224 and is configured to monitor the precision sensor reference voltage signal 223. The voltmeter 250 is configured to establish a sensor 210 operating point and more accurately interpret responses of the sensor 210. The voltmeter 250 also cooperates with non-inverting first operational amplifier 220 to buffer the precision sensor reference voltage signal 223 and apply a substantially accurate sensor reference voltage signal 226 to the first terminal 202. The second operational amplifier 230 is connected to the second terminal 204 through the second signal line 214 and is configured to receive current discharging therefrom in response to the accurate sensor reference voltage signal 226 applied to the first terminal 202.

The tunable second precision resistor 240 is connected between an output and an inverting input of o the second operational amplifier 230 and cooperates therewith to generate the sensor signal 234 that is substantially proportional to the glucose level of the patient's blood. The current is delivered to an inverting terminal of the second operational amplifier 230 having a non-inverting input 232 which is grounded, as shown in FIG. 8a. Accurate current measure (e.g., discharging from the second terminal 204) at the second operational amplifier 230 is established by the tunable second precision resistor 240. By configuring the glucose sensor 210 in this manner, the need for a microprocessor is eliminated and the associated calibration procedures and current drain. Output of the second operational amplifier 230 as determined by the precision sensor reference voltage 223 as well as by the sensor 210 operating point (i.e., glucose levels) and the second precision resistor 240, is then processed and transmitted upon request by the remote transponder 800.

Referring briefly to FIG. 8b, shown is a block diagram of the 3-pin glucose sensor 210 which is similar to the block diagram of the 2-pin glucose sensor 210 shown in FIG. 8a with the addition of a third terminal 206 (i.e., an auxiliary electrode) to the electrode assembly 201. The 3-pin glucose sensor 210 also includes an auxiliary control circuit 260. The third terminal 206 is co-located with the first and second terminals 204, 206 and is also preferably in fluid communication with the patient's blood. The auxiliary control circuit 260 is connected between the third terminal 206 and the second operational amplifier 230 through the third signal line 216 and is configured to monitor and control an amount of current discharging from the third terminal 206. The third terminal 206 is configured to divert current away from the second terminal 204 during application of the accurate sensor reference voltage signal 226 applied to the first terminal 202. The addition of the third terminal 206 to the electrode assembly 201 of the 3-pin glucose sensor 210 may help to reduce the consumption of silver and/or silver chloride contained in the second terminal 204 by drawing a portion of current away from the second terminal 204. In this manner, the third terminal 206 acts to stabilize the electrode potential and the operational life of the glucose sensor 210 may be increased.

Figure 5A:
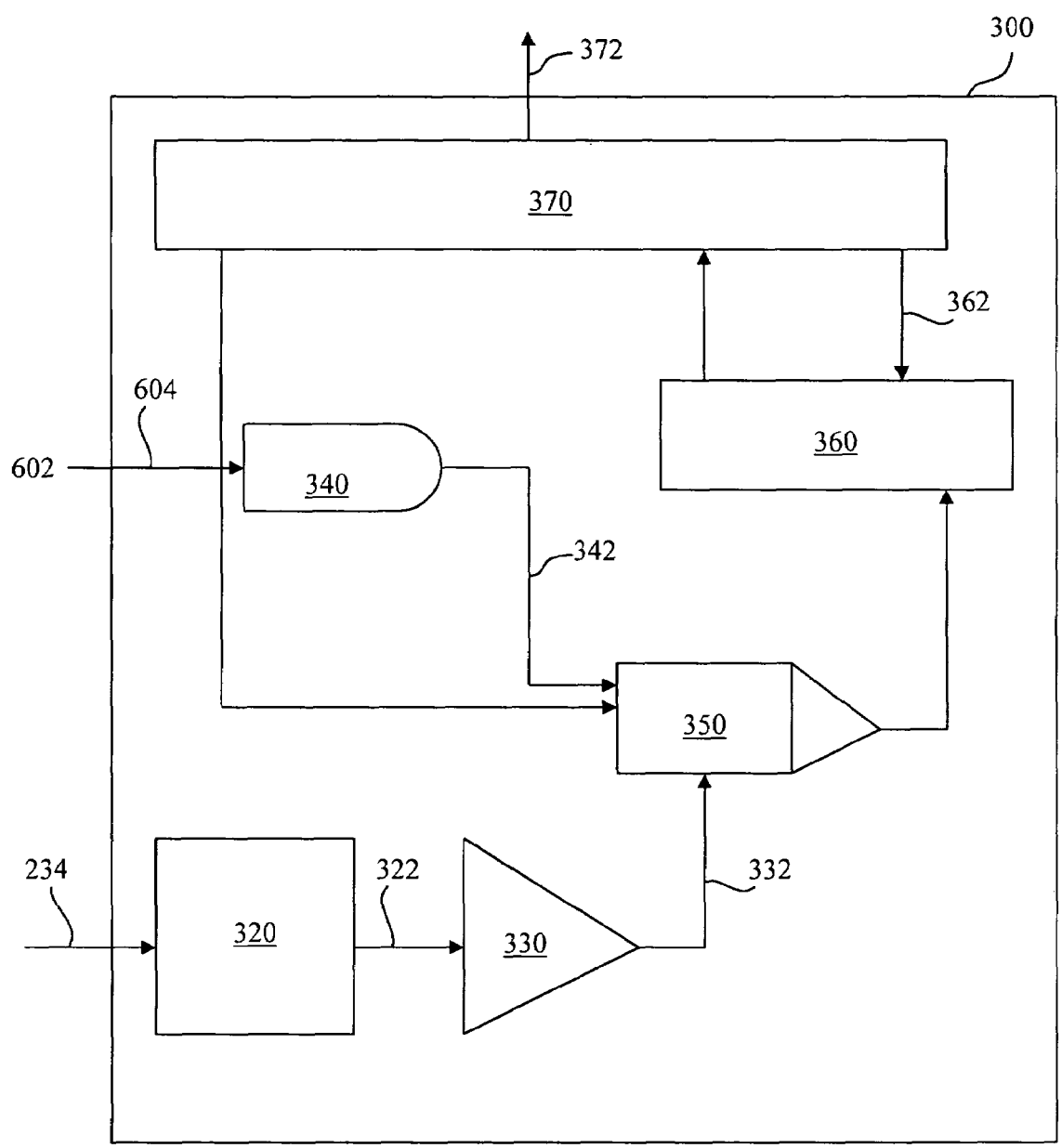
FIG. 5a is a block diagram of an analog-to-digital (A/D) assembly as may be included with the on-chip transponder for the embodiment of the bio-sensor system configured to receive a single one of the sensor signals.
Figure 5B:
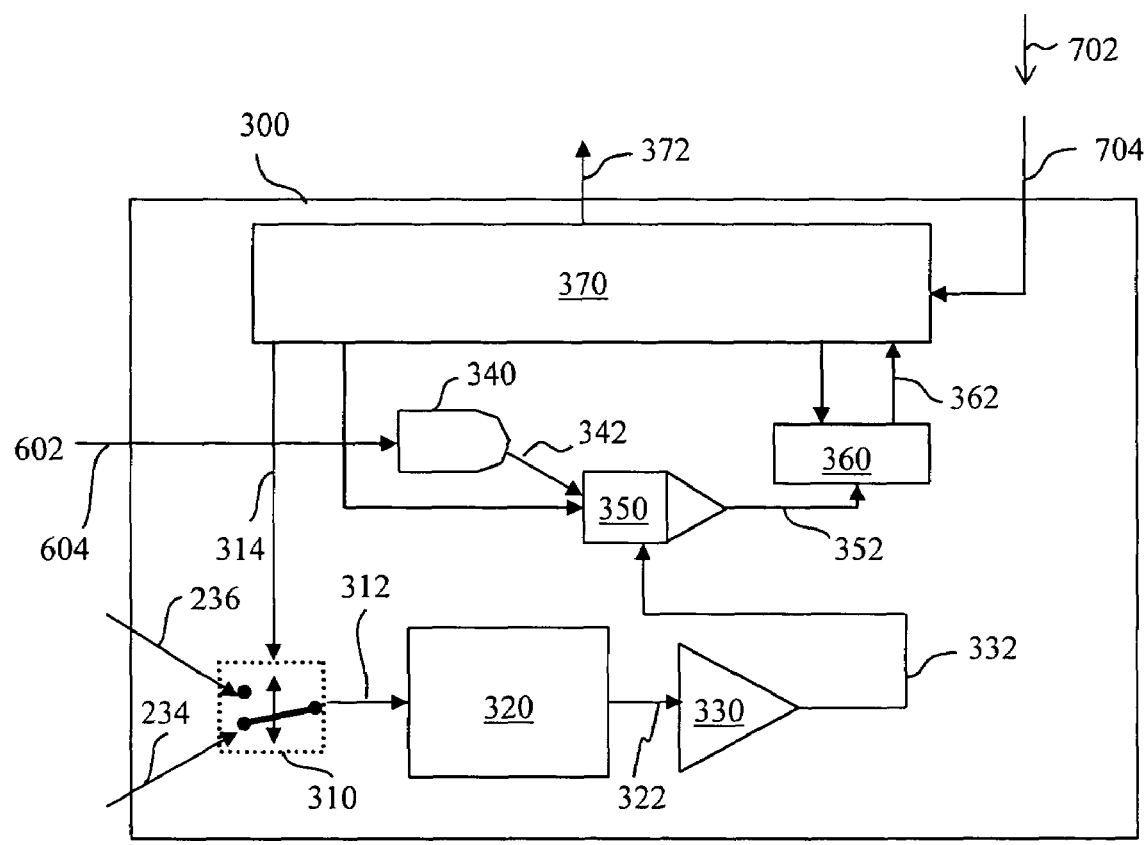
FIG. 5b is a block diagram of the A/D assembly as may be included with the on-chip transponder for the embodiment of the bio-sensor system that may include a switch for selecting a particular sensor signal from multiple sensors.

Referring now to FIGS. 5a and 5b, the architecture of the A/D assembly 300 will be described in detail. In general, the A/D assembly 300 is configured to convert the physiological parameter contained into an analog electrical signal which may be represented as current or voltage. The A/D assembly 300 may also perform encoding to include message encryption of the sensor signal 234, the addition of a unique identification code or message (e.g., to identify the particular sensor 210(s) from which the sensor signal(s) 234 originated). In addition, the A/D assembly 300 may include error detection and prevention bits with the sensor signal 234 to ensure the integrity of the sensor signal 234 (i.e., to verify that the data sent from the sensor 210 is equivalent to the data received).

Referring more specifically to FIG. 5a, shown is a block diagram of the A/D assembly 300 for the embodiment of the bio-sensor system 10 configured to receive the sensor signal 234 from a single sensor 210, such as from the glucose sensor 210. FIG. 5b is a block diagram of the A/D assembly 300 for the embodiment of the bio-sensor system 10 additionally including the switch 310 to allow for selection among a plurality of sensor signals 234 sent from a plurality of the sensors 210. In FIGS. 5a and 5b, common subcomponents of the A/D assembly 300 include a processor-filter 320, an amplifier 330, a voltage comparator 340, an A/D converter 350, a covert logic device 360 and a controller 370. The processor-filter 320 is connected to the sensor 210 and is configured to receive the sensor signal 234 therefrom. The sensor signal 234 is characterized by an analog voltage which, in the case of the glucose sensor 210, is substantially proportional to glucose concentration. The voltage may or may not have been processed in preparation for transmission to the remote transponder 800. In any case, further sensor signal 234 preparation may be required.

As shown in FIGS. 5a and 5b, the processor-filter 320 receives the sensor signal 234 and generates a filtered signal 322 in response thereto. The processor-filter 320 may perform biasing functions as well as measurement of the sensor 210 status. The processor-filter 320 may also strip off spectral components (e.g., high frequency noise spikes) from the sensor signal 234 as well as perform normalizing of the voltage levels to match the capabilities of the on-chip transponder 100. Additional functions may be performed by the processor-filter 320 such as averaging and other functions required to ensure accurate sampling of the sensor 210 data.

The amplifier 330 is connected to the processor-filter 320 and is configured to receive the filtered signal 322 therefrom and amplify the filtered signal 322 such that a minimum and maximum voltage of the signal is within the limits of the A/D converter 350 in order to provide maximum resolution of the digitized signal. Upon receiving the filtered signal 322, the amplifier 330 is configured to generate an amplified signal 332 in response to the filtered signal 322. The voltage comparator 340 is connected to the power supply 600 and is configured to receive the power signal 602 therefrom and generate a normalized voltage signal 342 in response thereto. More specifically, the voltage comparator 340 normalizes the A/D assembly 300 circuitry such that its operating conditions match the need of the sensor signal 234 to be digitized.

The normalized voltage signal 342 is then first sampled and then quantized by the A/D assembly 300 prior to digitization. This function is performed by the A/D converter 350 which is connected between the amplifier 330 and the voltage comparator 340. The A/D converter 350 is configured to receive the amplified signal 332 and the normalized voltage signal 342 and generate a converter signal 352 in response thereto. A single sample may be collected or multiple samples may be collected in order to provide a more accurate average or to track variations in the sensor signal 234 over a period of time (e.g., over several heartbeats of the patient within whom the sensor 210 may be implanted). The covert logic device 360 receives the converter signal 352 from the A/D converter 350. The covert logic device 360 is also in two-way communication with the controller 370 such that the covert logic device 360 receive the converter signal 352 and generates a logic signal 362 in response thereto. The covert logic device 360 may also contain error correction and/or voltage level-shift circuitry.

The controller 370 is configured to gate the A/D assembly 300 for synchronizing signal transmission with the data processor 400. As shown in FIG. 5a, the controller 370 is in two-way communication with the covert logic device 360. Referring to FIG. 5b for the embodiment of the bio-sensor system 10 including the RF receiver 700, the controller 370 is connected to the RF receiver 700 and receives the message signal 702 therefrom via message/control line 704. The RF receiver 700 also receives the logic signal 362 from the covert logic device 360 and is configured to synchronize the A/D converter 350 with the data processor 400 for subsequent generation of the digital signal 372 in response to the message signal 702 and the logic signal 362.

For embodiments of the bio-sensor system 10 including the plurality of sensors 210, the A/D assembly 300 further includes the switch 310 which is connected to the controller 370 via sensor selection line 314. The switch 310 is also connected to the processor-filter 320 via switch signal line 312. In such embodiments, the controller 370 is responsive to the message signal 702 and is operative to cause the switch 310 to select among a plurality of sensor signals 234 for subsequent transmission thereof to the processor-filter 320. As was earlier mentioned, in such configurations of the bio-sensor system 10 having multiple ones of the sensors 210, the data processor 400 may be configured to assign a preset identification code to the digital signal 372 for identifying the sensor 210 from which the sensor signal 234 originates. The digital signal 372 may be either a packet of serial data (i.e., a burst of data over a fixed duration) or a stream of data that lasts as long as information is requested by the remote transponder 800 depending on the contents of the message signal 702 transmitted to the controller 370 via the message/control line 704.

Figure 3:
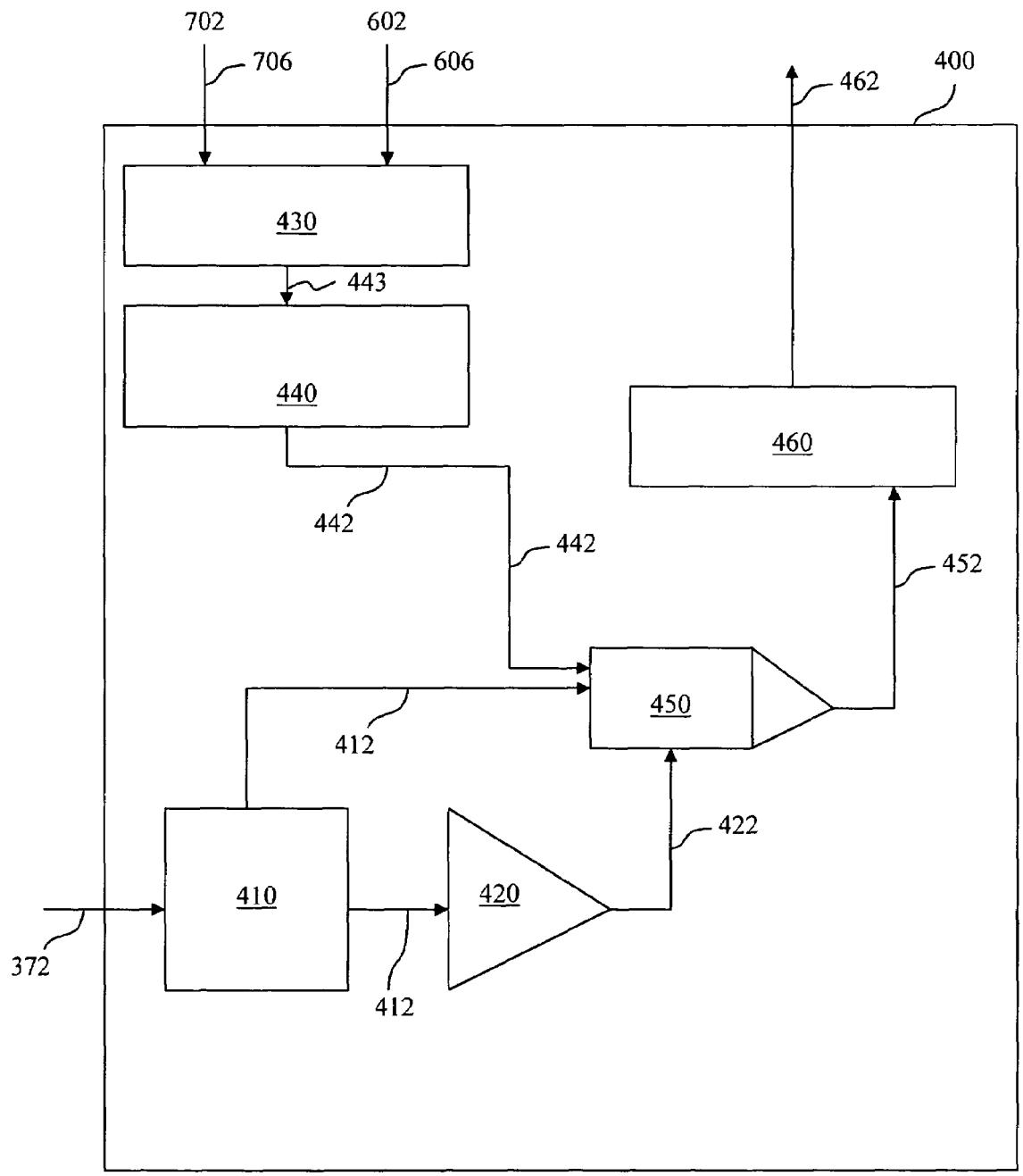
FIG. 3 is a block diagram of a data processor that may be included with the on-chip transponder.

Referring now to FIG. 3, the specific architecture of the data processor 400 will be described in detail. In general, the data processor 400 receives the digital signal 372 from the A/D assembly 300 and filters, amplifies and/or encodes the digital signal 372 to generate a processed data signal 462. Power to the data processor 400 is supplied via power line 606 to the program counter 430. If included, the RF receiver 700 transmits the message signal 702 to the program counter 430 via message/control line 706 to control and synchronize telemetry operations. The data processor 400 may be configured to gate the data signal 462 to determine when to transmit the data signal 462 to the remote transponder 800.

In addition, the data processor 400 may also be configured to sum the data signal 462 with other data (i.e., from other sensors 210). As can be seen in FIG. 3, the data processor 400 includes a signal filter 410, an amplifier 420, a program counter 430, an interrupt request device 442, a calculator 450 and a digital filter 460. The signal filter 410 is connected to the A/D assembly 300 and is configured to receive the digital signal 372 and remove unwanted noise or aliasing components that may be included as a result of conversion of the sensor signal 234 from analog to digital. The signal filter 410 ultimately generates a filtered signal 412. The filtered signal 412 is in digital format and is made up of a series of high and low voltages.

Still referring to FIG. 3, the amplifier 420 is connected to the signal filter 410 and is configured to receive the filtered signal 412 therefrom and generate an amplified signal 422 in response thereto. The amplifier 420 isolates the data processor 400 from the analog-to-digital conversion process and prepares the voltage level for a calculation stage. As was earlier mentioned, the program counter 430 is connected to the RF receiver 700 and the power supply 600 and is configured to receive respective ones of the message signal 702 and the power signal 602. The program counter 430 also generates a gated signal 432. The interrupt request device 442 is connected to the program counter 430 and is configured to receive the gated signal 432 and generate an interrupt request signal 442.

The calculator 450 is connected to the the amplifier 420 and the interrupt request device 442 and is configured to receive respective ones of the filtered signal 412, the amplified signal 422 and the gated signal 432 and generate an encoded signal 452. In this regard, the program counter 430, interrupt request device 442 and calculator 450 cooperate together in order to gate (i.e., start and stop) the signal and may additionally assign a unique message identification code (e.g., to identify the particular sensor(s) 210 from which the signal originated). In addition, error detection and prevention bits may be added to increase reliability and integrity of the signal by repeating a portion or all of the message in the same data packet. The digital filter 460 is connected to the calculator 450 and is configured to receive the encoded signal 452 therefrom and generate the data signal 462. The digital filter 460 shapes the series of high and low voltages that make up the digital signal 372 for subsequent modulation by the RF transmitter 500.

Figure 4:
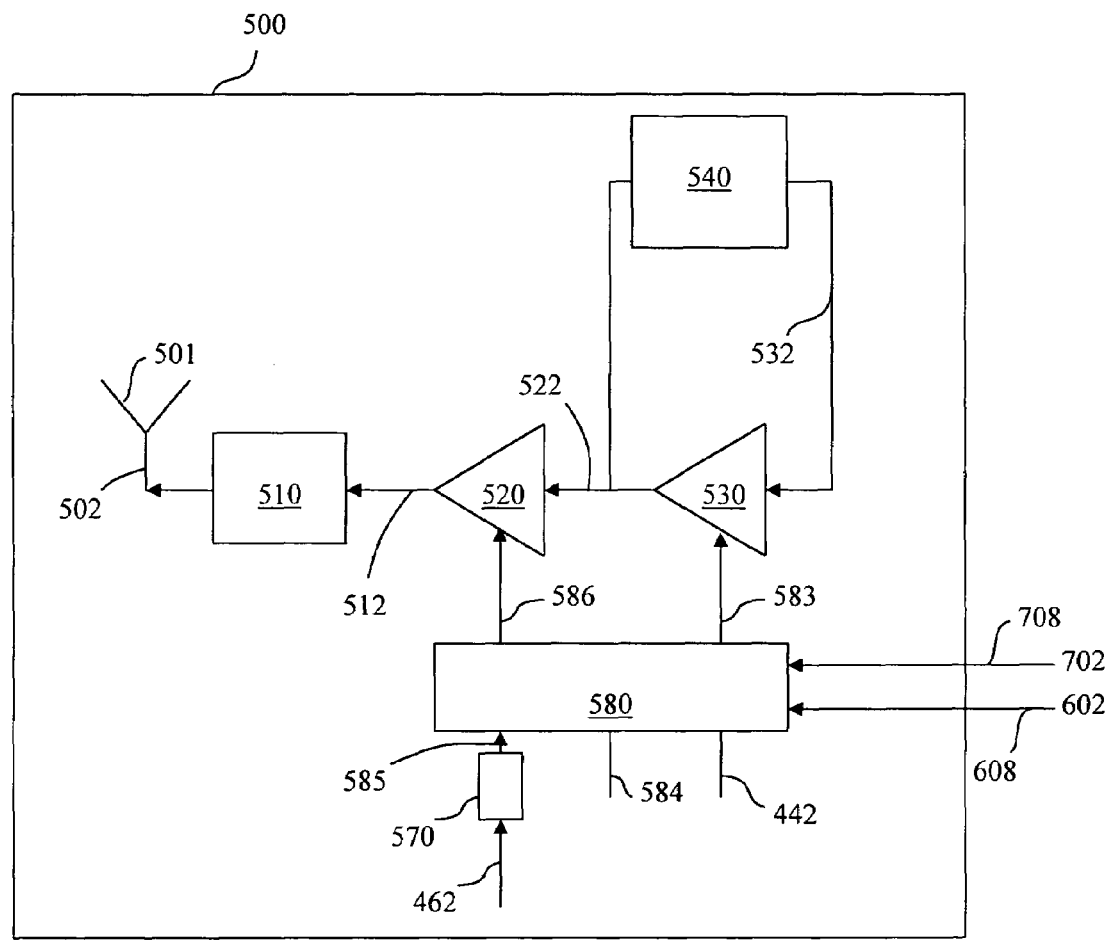
FIG. 4 is a block diagram of a radio frequency (RF) transmitter that may be included with the on-chip transponder.

Referring now to FIG. 4, the architecture of the RF transmitter 500 will be described in detail. In general, the RF transmitter 500 modulates the data signal 462 onto a radio carrier of a desired frequency, amplifies the modulated carrier and sends it to an RF transmitter antenna 501 for radiation to the remote transponder 800. Shown in FIG. 4 are subcomponents of the RF transmitter 500 comprising a data input filter 570, a modulator 580, a first transmitter amplifier 530, a transmitter filter 540, a second transmitter amplifier 520, a surface acoustic wave (SAW) filter 510 and the RF transmitter antenna 501. The RF transmitter 500 is powered upon receiving the power signal 602 at the modulator 580 from the power supply 600 via power line 608. If the bio-sensor includes the RF receiver 700, the message signal 702 is also received therefrom at the modulator 580 via message/control line 708. The data input filter 570 is connected to the data processor 400 and is configured to receive the data signal 462 therefrom to filter out high-frequency spectral components and generate a filtered data signal 585 in response thereto.

Referring still to FIG. 4, the modulator 580 is connected to the power supply 600, the RF receiver 700 and the data input filter 570 and is configured to pulse code modulate the filtered data signal 585 by varying an amplitude thereof and generating a first and second modulated signal 583, 586 in response thereto. The first transmitter amplifier 530 is connected to the modulator 580 and is configured to receive the first modulated signal 583 therefrom. The transmitter filter 540 generates a feedback signal 532 which is received by the first transmitter amplifier 530. The transmitter filter 540 cooperates with the first transmitter amplifier 530 to create a first amplified signal 522 at the desired frequency of radio transmission. The second transmitter amplifier 520 is connected to the modulator 580 and the first transmitter amplifier 530 and is configured to receive respective ones of the second modulated signal 586 and the first amplified signal 522 therefrom and generate a second amplified signal 512 having a desired power level that is preferably sufficient for reliable transmission to the remote transponder 800.

As shown in FIG. 4, the modulator 580 also receives input from enable control 582 input and modulation control 584 input to aid in performing the modulation function. The modulator 580 impresses (i.e., modulates via pulse-code modulation) the processed data in the data signal 462 onto the radio carrier via the first and second transmitter amplifiers 530, 520. The amplitude of the radio carrier is varied by the first and second modulated signals 583, 586. However, other well known modulation methods may be used to effect different cost, range, data rate, error rate and frequency bands. The SAW filter 510 is connected to the second transmitter amplifier 520 and is configured to receive the second amplified signal 512 and remove unwanted harmonics that may lie outside the allocated frequency spectrum for the type of radio service utilized by the bio-sensor system 10. The SAW filter 510 generates a transmitted signal 502 in response to the second amplified signal 512. The RF transmitter antenna 501 is connected to the SAW filter 510. The transmitted signal 502 is passed to the RF transmitter antenna 501 which is configured to radiate the transmitted signal 502 for receipt by the receiving antenna 801 of the remote transponder 800.

Figure 6:
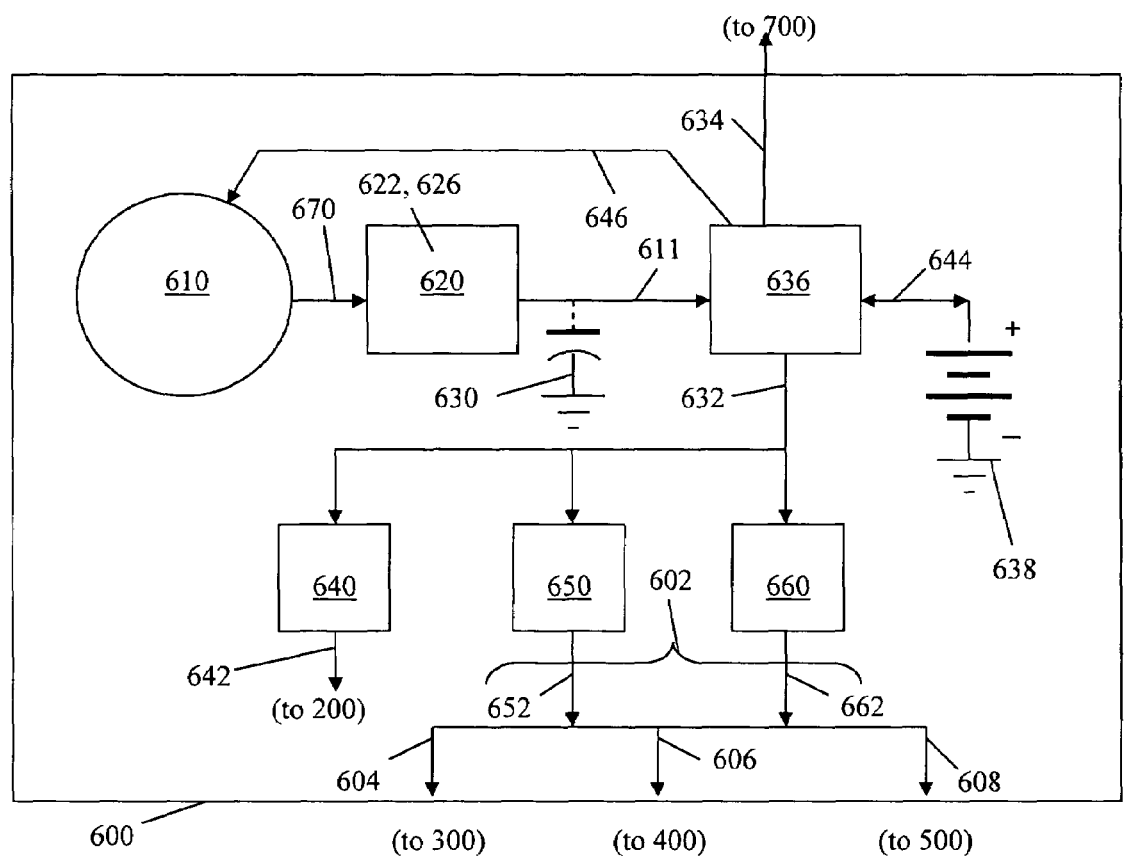
FIG. 6 is a block diagram of a power supply that collects voltage pulses from an electro-active polymer that may be embedded in muscle tissue for generating power for the on-chip transponder.

Referring now to FIG. 6, the circuit architecture of the power supply 600 will be described in detail. As was earlier mentioned, the power supply 600 includes the EAP generator 610 which is specifically adapted to generate the power signal 602 for powering the major components of the on-chip transponder 100 as well as provide the substantially stable and precise voltage to the sensor assembly 200. The power signal 602 is delivered to the A/D assembly 300, data processor 400 and RF transmitter 500 via power lines 604, 606, 608. As shown in FIG. 6, the subcomponents of the power supply 600 include the EAP generator 610, a pulse recovery circuit 620, a storage device 630, a controller 636, a battery 638, a first regulator 650, a second regulator 660 and a sensor reference supply 640.

Referring now more particularly to FIG. 6, the specific circuit architecture and operation of the power supply 600 will now be described. In a broad sense, the power supply 600 is configured to collect periodic power pulses from the EAP generator 610 that may preferably be embedded in muscle tissue of the type that moves on a substantially regular basis such as the periodic movement that accompanies breathing. The periodic power pulses are accumulated in the rechargeable battery 638 which powers the RF receiver 700 if, included, during standby mode wherein the RF receiver 700 "listens" for an interrogation request (i.e., scanner signal 882) from the remote transponder 800. Upon receiving the scanner signal 882, the power supply 600 provides power to remaining components of the on-chip transponder 100 to measure, process and transmit the requested data back to the remote transponder 800.

The EAP generator 610 is preferably positioned and oriented in muscle tissue such that the EAP generator 610 undergoes cycles of mechanical flexing and unflexing. In the case of breathing, the flex-unflex cycle may occur on the order of about once every six seconds depending on the breathing rate of the patient. In response to each flex-unflex cycle, the EAP generator 610 generates periodic alternating current (AC) voltage pulses 670. It is estimated that the power contained in each AC voltage pulse 670 may be on the order of about 0.2 Joules/gram of EAP material, depending on variables such as material type and flex parameters (e.g., duration of cycle, degree of flex, etc.). It is expected that the size of each AC voltage pulse 670 may be about one-hundred Volts or higher. However, the power supply 600 may be configured to generate the power signal 602 in response to relatively low-level AC voltage pulses 670.

The pulse recovery circuit 620 is connected to the EAP generator 610 and is configured to receive the AC voltage pulses 670 therefrom. Each one of the AC voltage pulses 670 is provided as alternating current with positive and negative current flow. A rectifier 622 may be included in the pulse recover circuit 620. The rectifier 622 may sum the positive and negative currents of the AC voltage pulses 670 into a single electrical direction to allow only positive currents to flow into the storage device 630. Half-wave (i.e., a diode) or full-wave (i.e., a diode bridge) rectifier circuits, well known in the art, may be utilized to sum the positive and negative currents into a generally course direct current (DC) voltage. The course DC voltage passes to the storage device 630. The storage device 630, which may be a filter capacitor, is configured to collect the pulse energy and store the voltage over many cycles for release as a substantially smooth DC voltage signal in response thereto. Optionally, a step-down (DC-DC) voltage converter 626 may be included in the pulse recovery circuit to reduce relatively high-levels of the AC voltage pulses 670 to a level suitable for charging the battery 638.

The controller 636 is connected to the storage device 630 and is configured to receive the substantially smooth DC voltage signal therefrom and generate a battery current 644. The controller 636 operates much like an automotive voltage regulator in that the controller 636 sends the battery current 644 to the battery 638 for charging thereof. In addition, the controller 636 is configured to receive current from the battery 638 for supplying a DC voltage signal 632 to the first and second regulators 650, 660 to create the power signal 602 for powering the A/D assembly 300, the data processor 400 and the RF transmitter 500. The controller 636 also delivers the DC voltage signal 632 to the sensor reference supply 640 for generating the sensor reference voltage signal 642 for powering the sensor 200. Furthermore, the controller 636 may be configured to generate and/or control a standby power signal 634 to continuously power the RF receiver 700 such that the RF receiver 700, if included, may detect the scanner signal 882. A voltage regulator that may be internal to the controller 636 may generate the standby power signal. Alternatively, the standby power signal 634 may be generated by one of the first and second voltage regulators 650, 660.

In addition, the controller 636 may provide current for biasing of the EAP generator 610 wherein current flowing from the battery 638 may be "stepped up" to a higher voltage level (e.g., 100 volts or higher) using a DC-DC voltage converter to generate a EAP biasing voltage 646. The EAP biasing voltage 646, which may be on the order of 3000 volts, may be provided across terminals of the EAP generator 610. Providing the EAP biasing voltage 646 to the EAP generator 610 is similar to the technique of charging an ignition coil of an automobile engine. In this regard, supplying the EAP biasing voltage 646 to the EAP generator 610 creates a charge condition that enables a greater output of the AC voltage pulses 670 than would be available without the EAP biasing voltage 646. It is estimated that the EAP biasing voltage 646 may be about 10-15 percent of actual output of the EAP generator 610.

The battery 638 is connected to the controller 636 and is configured to be charged by the battery current 644. In addition, the battery 638 and the controller 636 cooperate to generate the DC voltage signal 632. The battery 638 is also configured to store sufficient charge and supply sufficient current to the controller 636 for generating the standby power signal 634 for delivery to the RF receiver 700. In addition, the battery 638 is preferably configured to store and deliver sufficient current to the controller 636 for multiple transmission cycles wherein data is transmitted from the on-chip transponder 100 to the remote transponder 800. If necessary, the battery 638 also supplies the EAP biasing voltage 646 to the EAP generator 610. The battery 638 is rechargeable and may be fabricated of Lithium or other suitable materials to provide a lengthy lifetime.

As was earlier mentioned, the first regulator 650 is connected to the controller 636 and is configured to receive the DC voltage signal 632 therefrom and generate a first voltage signal 652 to power the A/D assembly 300, the data processor 400 and the RF transmitter 500. The second regulator 660 is also connected to the controller 636 and is configured to receive the DC voltage signal 632 therefrom and generate a second voltage signal 662 to power the A/D assembly 300, the data processor 400 and the RF transmitter 500. The first and second regulators 650, 660 create the smooth first and second voltage signals 652, 662 to form the power signal 602 at a specific voltage level as required by the on-chip transponder 100, independent of proximity of the remote transponder 800 to the on-chip transponder 100. Power signal 602 is delivered to the A/D assembly 300, the data processor 400 and the RF transmitter 500 via power lines 604, 606, 608. The sensor reference supply 640 is connected to the filter 630 and is configured to receive the DC voltage signal 632 therefrom and generate a sensor reference voltage signal 642 to supply power to the sensor assembly 200.

Figure 7:
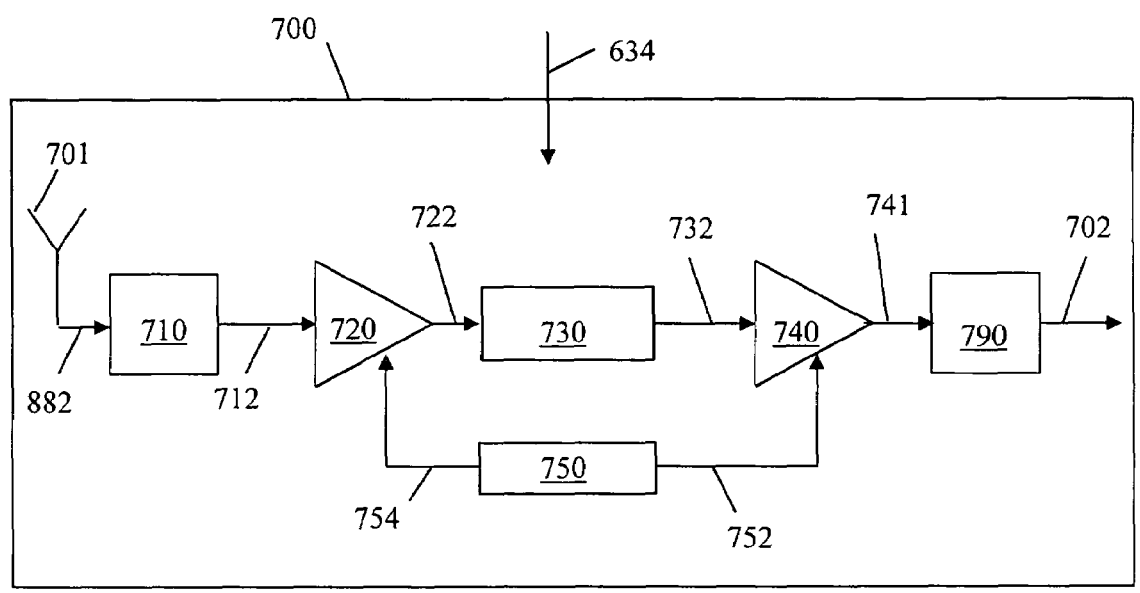
FIG. 7 is a block diagram of an RF receiver that may be included with the on-chip transponder.

Referring briefly to FIG. 7, shown is a block diagram of the RF receiver 700 that may be included with the on-chip transponder 100. In general, the RF receiver 700 continuously receives the standby power signal from the power supply. Upon receiving the scanner signal 882, the RF receiver 700 decodes the scanner signal 882 and alerts the on-chip transponder 100 that a request for data has been made. The decoded data informs the A/D assembly 300, the data processor 400 and the RF transmitter 500 as to which data is to be sent and when to send the data. In general, the RF receiver 700 reverses all transmitter steps that are performed by the RF transmitter 500. Subcomponents of the RF receiver 700 include an RF receiver antenna 701, a SAW filter 710, a first RF amplifier 720, a SAW delay 730, a second RF amplifier 740, a pulse generator 750 and a detector-filter 790. The RF receiver antenna 701 is configured to receive the scanner signal 882 from the remote transponder 800. The SAW filter 710 is connected to the RF receiver antenna 701 and is configured to receive the scanner signal 882 therefrom and filter the scanner signal 882 of unwanted signals that may overdrive or interfere with the operation of the RF receiver 700.

The SAW filter 710 generates a filtered scanner signal 712 in response thereto. The filtered scanner signal 712 may be weak after filtering and is therefore boosted (i.e., amplified) by the first RF amplifier 720 to a level that may be detected by demodulation circuitry. The demodulation componentry is comprised of the SAW delay 730, the second RF amplifier 740 and the pulse generator 750 connected as shown in FIG. 7. In general, the demodulating componentry cooperates to recover data contained in the scanner signal 882. The first RF amplifier 720 is connected to the SAW filter 710 and is configured to receive the filtered scanner signal 712 therefrom and generate a first amplified RF signal 722 in response thereto. The SAW delay 730 is connected to the first RF amplifier 720 and is configured to receive the first amplified RF signal 722 therefrom and generate a compared signal 732.

The second RF amplifier 740 is connected to the SAW delay 730 and is configured to receive the compared signal 732 therefrom. The pulse generator 750 is connected in parallel to the SAW delay 730 at the first and second RF amplifiers 720, 740 and cooperates therewith to generate first and second pulse signals 752, 754 for receipt by respective ones of the first and second RF amplifiers 720, 740 such that the second RF amplifier 740 generates a second amplified RF signal 741. The detector-filter 790 is connected to the second RF amplifier 740 and is configured receive the second amplified RF signal 741 therefrom and extract data from the scanner signal 882 and generate the message signal 702. The message signals 702 are passed to telemetry blocks of the A/D assembly 300, the data processor 400 and the RF transmitter 500 via message/control lines 704, 706, 708 to alert the blocks that a sensor 210 reading has been requested. The message/control lines 704, 706, 708 also convey and transmit/receive coordination and sensor 210 selection for configurations where the bio-sensor system 10 includes multiple ones of the sensors 210.

Referring now to FIG. 2, the circuit architecture of the remote transponder 800 will be described in detail. As shown, the remote transponder 800 may include transmitting subcomponents for transmitting data to the on-chip transponder 100 as well as receiving subcomponents for receiving the data contained in the data signal 462 which is transmitted by the on-chip transponder 100. The transmitting subcomponents may comprise an oscillator 860, an encoder 870, a power transmitter 880 and a transmitting antenna 883. The oscillator 860 is configured to generate an analog signal 862 at a predetermined frequency. The encoder 870 is connected to the oscillator 860 and is configured to receive and modulate the analog signal 862 and generate an encoded signal 872 in response thereto. The power transmitter 880 is connected to the encoder 870 and is configured to receive and amplify the encoded signal 872 and generate the scanner signal 882. The transmitting antenna 883 is connected to the power transmitter 880 and is configured to receive the scanner signal 882 therefrom for radio transmission to the on-chip transponder 100.

Referring still to FIG. 2, the remote transponder 800 may also include the receiving subcomponents to allow receiving of the scanner signal 882 from the on-chip transponder 100. The receiving subcomponents of the remote transponder 800 are structurally and functionally equivalent to the RF receiver 700 as shown in FIG. 7 and as described above. The receiving components of the remote transponder 800 may comprise a receiving antenna 801, a SAW filter 810, a first RF amplifier 820, a SAW delay 830, a second RF amplifier 840, a pulse generator 850 and a detector-filter 890. The receiving antenna 801 is configured to receive the transmitted signal 502 from the RF transmitter 500. The SAW filter 810 is connected to the receiving antenna 801 and is configured to receive and filter the transmitted signal 502 of unwanted signals that may interfere with the remote transponder 800 and generate a filtered RF signal 812 in response thereto. The first RF amplifier 820 is connected to the SAW filter 810 and is configured to receive the filtered RF signal 812 therefrom and generate a first amplified RF signal 822 in response thereto.

The SAW delay is connected to the first RF amplifier 820 and is configured to receive the first amplified RF signal 822 therefrom and generate a compared signal 832. The second RF amplifier is connected to the SAW delay 830 and is configured to receive the compared signal 832 therefrom. The pulse generator is connected in parallel to the SAW delay 830 at the first and second RF amplifiers 820, 840 and cooperates therewith to generate first and second pulse signals 852, 854 for receipt by respective ones of the first and second RF amplifiers 820, 840 such that the second RF amplifier generates 840 a second amplified RF signal 841. The detector-filter 890 is connected to the second RF amplifier and is configured receive the second amplified RF signal 841 for extraction of digitized data therefrom.

As is also shown in FIG. 2, the bio-sensor system 10 may further include a decoder 900 connected to the detector-filter 890 by data output lines 902, 904 and configured to receive the second amplified RF signal 841 for extraction of digitized data therefrom. For configurations of the bio-sensor system 10 having the plurality of sensors 210 wherein each one of the sensor 210 is operative to sense a physiological parameter of the patient and generate the sensor signal 234 in response thereto, the decoder 900 may be configured to select one from among the plurality of sensor signals 234 from which to receive data.

The decoder 900 may be configured to convert the digitized data back to original physiological data. The decoder 900 may also check the second amplified RF signal 841 for errors such that an operator may be notified whether or not the telemetry message was successfully received. The decoder 900 allows the sensor signal 234 data to be displayed on the remote transponder 800 such as a handheld device. Alternatively, the sensor signal 234 data may be stored in a computer database. The database may add a time stamp and patient information in order to make a complete record of the telemetry event. Combined with other records, trends and behavior may be graphed and analyzed.

Referring now to FIGS. 1 and 2, the operation of the bio-sensor system 10 will now be generally described. More specifically, the method of remotely monitoring physiological parameters using the bio-sensor system 10 will be described wherein the bio-sensor system 10 broadly comprises the remote transponder 800 and the on-chip transponder 100 having the sensor 210 and which is implantable in the patient. As was earlier mentioned, the power supply 600 includes the EAP generator 610 which is embedded in muscle tissue of the patient such the power supply 600 may generate the power signal 602 for powering the on-chip transponder 100 upon receipt of the scanner signal 882 from the remote transponder 800.

The method comprises the steps of remotely generating and wirelessly transmitting the scanner signal 882 with the remote transponder 800 wherein the scanner signal 882 contains the telemetry data request. The scanner signal 882 is received at the on-chip transponder 100 whereupon the scanner signal 882 is filtered, amplified and demodulated to generate the message signal 702. The RF receiver 700 receives the standby power signal 634 from the power supply 600 to enable the RF receiver 700 to continuously "listen" for the scanner signal 882.

Upon receipt of the scanner signal 882, the power signal 602 is generated at the power supply 600 in the manner as was earlier described. Upon being powered by the sensor reference voltage signal 642, the sensor 210 senses at least one physiological parameter of the patient in the manner as was described above and generates the analog sensor signal 234. The power signal 602, the analog sensor signal 234 and the message signal 702 are all received at the A/D assembly 300 which then generates the digital signal 372 which is representative of the analog sensor signal. The power signal 602, the message signal 702 and the digital signal 372 are then received at the data processor 400 which prepares the digital signal 372 for modulation. The data processor 400 then generates the data signal 462 which is representative of the digital signal 372. The power signal 602, the message signal 702 and the data signal 462 are received at the RF transmitter 500 which then modulates, amplifies, filters and wirelessly transmits a transmitted signal 502 from the on-chip transponder 100. The remote transponder 800 then received the transmitted signal 502 from the on-chip transponder 100 and extracts data that is representative of the physiological parameter of the patient.

Referring briefly to FIG. 8a, wherein the sensor 210 is configured as the 2-pin glucose sensor 210, the method may further comprise steps for enhancing the stability and precision of the power supplied to the electrode assembly 201 by first tuning the power signal 602 with the first precision resistor 224 to generate the sensor reference voltage signal 642 at the level of about positive 0.7 volts. The sensor reference voltage signal 642 is received at the first operational amplifier 220 which generates the precision sensor reference voltage signal 223. The voltmeter 250 monitors the precision sensor reference voltage signal to establish a sensor 210 operating point. The first operational amplifier 220 cooperates with the voltmeter 250 to buffer the precision sensor reference voltage signal 223 in order to generate a substantially accurate sensor reference voltage signal 226.

The accurate sensor reference voltage signal 226 is applied to the first terminal 202 to cause the reaction with the patient's blood which causes current to discharge from the second terminal 204 in the manner earlier described. The current discharges at the second terminal 204 in proportion to the glucose level. By tuning the second precision resistor 240, which is connected in series to the second operational amplifier 230, a voltage divider is formed with the glucose sensor 210. The second precision resistor 240, in cooperation with the second operational amplifier 230, measures the level of discharging current and generates the sensor signal 234 which is substantially proportional to the glucose level of the patient.

Referring briefly to FIG. 8b, for the case where the sensor 210 is a 3-pin glucose sensor 210 including the third terminal 206 that is co-located with the first and second terminals 204, 206, the method of sensing the glucose level further comprises the steps of diverting a portion of the current away from the second terminal 204. This is performed by discharging current at the third terminal 206 during application of the accurate sensor reference voltage signal 226 to the first terminal 202. The current from the third terminal 206 is passed through the auxiliary control circuit 260 which is connected between the third electrode and the second operational amplifier 230. The auxiliary control circuit 260 monitors and controls the amount of current discharging from the third terminal 206 in order to stabilize the accurate sensor reference voltage signal 226 applied to the first terminal 202 which may increase the operational life of the glucose sensor 210.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A bio-sensor system powered by an electro-active polymer (EAP) generator and being adapted to provide a substantially stable voltage to a sensor assembly that is implantable in a patient such that physiological Parameters thereof may be accurately measured, the bio-sensor system comprising:

a remote transponder configured to transmit a scanner signal to an implantable on-chip transponder and to receive a data signal therefrom;

the implantable on-chip transponder in wireless communication with the remote transponder and being configured to receive the scanner signal and transmit the data signal, the on-chip transponder including:

a sensor being configured to generate a sensor signal representative of the physiological parameter of the patient;

a power supply having the EAP generator adapted to be embedded in muscle tissue of the patient and configured to generate a power signal for powering the on-chip transponder;

an analog-to-digital (A/D) assembly connected to the power supply and the sensor, the A/D assembly being configured to respectively receive the power signal and the sensor signal and generate a digital signal in response thereto;

a data processor connected to the A/D assembly and the power supply, the data processor being configured to respectively receive the power signal and the digital signal and generate a data signal in response thereto; and a radio frequency (RE) transmitter connected to the power supply and the data processor and being configured to respectively receive the power signal and the data signal and to modulate, amplify, filter and transmit the data signal;

wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter;

wherein the sensor is a glucose sensor having an electrode assembly adapted to be in fluid communication with the patient's blood and being configured to measure a glucose level thereof;

wherein the sensor reference voltage is supplied to the electrode assembly at a substantially constant value of about positive 0.7 volts;

wherein the glucose sensor is a 2-pin glucose sensor with the electrode assembly having first and second terminals adapted to be in fluid communication with the patient's blood, the glucose sensor further including:

a first precision resistor connected to the power supply and configured to receive the sensor reference voltage therefrom for excitation of the glucose sensor;

a first operational amplifier connected to the first precision resistor and being configured to receive the sensor reference voltage therefrom and generate a precision sensor reference voltage in response thereto;

a voltmeter connected to the first operational amplifier and the first precision resistor and being configured to monitor the precision sensor reference voltage and establish a sensor operating point, the first operational amplifier and the voltmeter cooperating to buffer the precision sensor reference voltage and apply a substantially accurate sensor reference voltage to the first terminal;

a second operational amplifier connected to the second terminal and being configured to receive current discharging therefrom in response to the accurate sensor reference voltage applied to the first terminal; and a tunable second precision resistor connected to the second operational amplifier and cooperating therewith to generate a sensor signal that is substantially proportional to the glucose level of the patient's blood.

2. The bio-sensor system of claim 1 wherein the glucose sensor is a 3-pin glucose sensor with the electrode assembly further including a third terminal co-located with the first and second terminals and adapted to be in fluid communication with the patient's blood, the glucose sensor further including:

an auxiliary control circuit connected between the third electrode and the second operational amplifier and being configured to monitor and control an amount of current discharging from the third terminal;

wherein the third terminal is configured to divert current away from the second electrode during application of the accurate sensor reference voltage applied to the first terminal such that the operational life of the glucose sensor may be increased.

3. A bio-sensor system powered by an electro-active polymer (EAP) generator and being adapted to provide a substantially stable voltage to a sensor assembly that is implantable in a patient such that physiological parameters thereof may be accurately measured, the bio-sensor system comprising:

a remote transponder configured to transmit a scanner signal to an implantable on-chip transponder and to receive a data signal therefrom;

the implantable on-chip transponder in wireless communication with the remote transponder and configured to receive the scanner signal and to transmit the data signal, the on-chip transponder including:

a sensor being configured to generate a sensor signal representative of the physiological parameter of the patient;

a power supply having the EAP generator adapted to be embedded in muscle tissue of the patient and being configured to generate a power signal for powering the on-chip transponder;

a radio frequency (RF) receiver configured to receive the power signal and the scanner signal and to filter, amplify and demodulate the scanner signal and generate a message signal for controlling the on-chip transponder;

an analog-to-digital (A/D) assembly connected to the power supply, the RF receiver and the sensor, the A/D assembly being configured to respectively receive the power signal, the sensor signal and the message signal and generate a digital signal in response thereto;

a data processor connected to the A/D assembly, the power supply and the RF receiver, the data processor being configured to respectively receive the power signal, the digital signal and the message signal and generate a data signal in response thereto; and an RF transmitter connected to the power supply, the data processor and the RF receiver and being configured to respectively receive the power signal, the data signal and the message signal and to modulate, amplify, filter and transit the data signal;

wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter, wherein the sensor is a glucose sensor having an electrode assembly adapted to be in fluid communication with the patient's blood and being configured to measure a glucose level thereof;

wherein the sensor reference voltage being supplied to the electrode assembly at a substantially constant value of about positive 0.7 volts;

wherein the glucose sensor is a 2-pin glucose sensor with the electrode assembly having first and second terminals adapted to be in fluid communication with the patient's blood, the glucose sensor further including:

a first precision resistor connected to the power supply and configured to receive the sensor reference voltage therefrom for excitation of the glucose sensor;

a first operational amplifier connected to the first precision resistor and being configured to receive the sensor reference voltage therefrom and generate a precision sensor reference voltage in response thereto;

a voltmeter connected to the first operational amplifier and the first precision resistor and being configured to monitor the precision sensor reference voltage and establish a sensor operating point, the first operational amplifier and the voltmeter cooperating to buffer the precision sensor reference voltage and apply a substantially accurate sensor reference voltage to the first terminal;

a second operational amplifier connected to the second terminal and being configured to receive current discharging therefrom in response to the accurate sensor reference voltage applied to the first terminal; and a tunable second precision resistor connected to the second operational amplifier and cooperating therewith to generate a sensor signal that is substantially proportional to the glucose level of the patient's blood.

4. The bio-sensor system of claim 3 wherein the glucose sensor is a 3-pin glucose sensor with the electrode assembly further including a third terminal co-located with the first and second terminals and adapted to be in fluid communication with the patient's blood, the glucose sensor further including:

an auxiliary control circuit connected between the third electrode and the second operational amplifier and being configured to monitor and control an amount of current discharging from the third terminal;

wherein the third terminal is configured to divert current away from the second electrode during application of the accurate sensor reference voltage applied to the first terminal such that the operational life of the glucose sensor may be increased.

5. A bio-sensor system powered by an electro-active polymer (EAP) generator and being adapted to provide a substantially stable voltage to a sensor assembly that is implantable in a patient such that physiological parameters thereof may be accurately measured, the bio-sensor system comprising:

a remote transponder configured to transmit a scanner signal to an implantable on-chip transponder and to receive a data signal therefrom;

the implantable on-chip transponder in wireless communication with the remote transponder and configured to receive the scanner signal and to transmit the data signal, the on-chip transponder including:

a sensor being configured to generate a sensor signal representative of the physiological parameter of the patient;

a power supply having the EAP generator adapted to be embedded in muscle tissue of the patient and being configured to generate a power signal for powering the on-chip transponder;

a radio frequency (RF) receiver configured to receive the power signal and the scanner signal and to filter, amplify and demodulate the scanner signal and generate a message signal for controlling the on-chip transponder;

an analog-to-digital (A/D) assembly connected to the power supply, the RF receiver and the sensor, the A/D assembly being configured to respectively receive the power signal, the sensor signal and the message signal and generate a digital signal in response thereto;

a data processor connected to the A/D assembly, the power supply and the RF receiver, the data processor being configured to respectively receive the power signal, the digital signal and the message signal and generate a data signal in response thereto; and an RF transmitter connected to the power supply, the data processor and the RF receiver and being configured to respectively receive the power signal, the data signal and the message signal and to modulate, amplify, filter and transit the data signal;

wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter;

wherein the A/D assembly includes:

a processor-filter connected to the bio-sensor and being configured to receive the sensor signal therefrom and generate a filtered signal in response thereto;

an amplifier connected to the processor-filter and being configured to receive the filtered signal therefrom and generate an amplified signal in response thereto;

a voltage comparator connected to the power supply and being configured to receive the power signal therefrom and generate a normalized voltage signal in response thereto;

an A/D converter connected to the amplifier and the voltage comparator and being configured to receive respective ones of the amplified signal and the normalized voltage signal therefrom and generate a converter signal in response thereto;

a covert logic device connected to the A/D converter and being configured to receive the converter signal therefrom and generate a logic signal in response thereto; and a controller in two-way communication with the RF receiver and being connected to the covert logic device, the controller being configured to receive the message signal and the logic signal and to synchronize the A/D converter with the data processor for subsequent generation of the digital signal in response to the message signal and the logic signal.

6. The bio-sensor system of claim 5 further including:
a plurality of sensors, each one of the sensors being operative to sense a distinct physiological parameter of the patient and generate a sensor signal representative thereof;
wherein the A/D assembly further includes a switch connected to the controller with the controller being responsive to the message signal and being operative to cause the switch to select among sensor signals for subsequent transmission thereof to the processor-filter.

7. The bio-sensor system of claim 6 wherein the data processor includes:
a signal filter connected to the A/D assembly and being configured to receive the digitized signal therefrom, remove unwanted noise and generate a filtered signal in response thereto;
an amplifier connected to the signal filter and being configured to receive the filtered signal and generate an amplified signal in response thereto;
a program counter connected to the RF receiver and the power supply and being configured to receive respective ones of the message signal and the power signal therefrom and generate a gated signal in response thereto;
an interrupt request device connected to the program counter and being configured to receive the gated signal therefrom and generate an interrupt request signal in response thereto;
a calculator connected to the signal filter, the amplifier and the interrupt request device and being configured to receive respective ones of the filtered signal, the amplified signal and the gated signal therefrom and generate an encoded signal in response thereto; and
a digital filter connected to the calculator and being configured to receive the encoded signal therefrom and generate the data signal in response thereto.

8. A bio-sensor system powered by an electro-active polymer (EAP) generator and being adapted to provide a substantially stable voltage to a sensor assembly that is implantable in a patient such that physiological parameters thereof may be accurately measured, the bio-sensor system comprising:
a remote transponder configured to transmit a scanner signal to an implantable on-chip transponder and to receive a data signal therefrom;
the implantable on-chip transponder in wireless communication with the remote transponder and configured to receive the scanner signal and to transmit the data signal, the on-chip transponder including:
a sensor being configured to generate a sensor signal representative of the physiological parameter of the patient;
a power supply having the EAP generator adapted to be embedded in muscle tissue of the patient and being configured to generate a power signal for powering the on-chip transponder;
a radio frequency (RF) receiver configured to receive the power signal and the scanner signal and to filter, amplify and demodulate the scanner signal and generate a message signal for controlling the on-chip transponder;
an analog-to-digital (A/D) assembly connected to the power supply, the RF receiver and the sensor, the A/D assembly being configured to respectively receive the power signal, the sensor signal and the message signal and generate a digital signal in response thereto;
a data processor connected to the A/D assembly, the power supply and the RF receiver, the data processor being configured to respectively receive the power signal, the digital signal and the message signal and generate a data signal in response thereto; and
an RF transmitter connected to the power supply, the data processor and the RF receiver and being configured to respectively receive the power signal, the data signal and the message signal and to modulate, amplify, filter and transit the data signal;
wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter;
wherein the RF transmitter includes:
a data input filter connected to the data processor and being configured to receive the data signal therefrom to filter out high-frequency spectral components and generate a filtered data signal in response thereto;
a modulator connected to the power supply, the RF receiver and the data input filter and being configured to receive respective ones of the message signal, the power signal and the filtered data signal therefrom and to pulse code modulate the filtered data signal by varying amplitude thereof and generating a first and second modulated signal in response thereto;
a first transmitter amplifier connected to the modulator and being configured to receive the first modulated signal therefrom;
a transmitter filter cooperating with the first transmitter amplifier to create a first amplified signal at a desired frequency of radio transmission;
a second transmitter amplifier connected to the modulator and the first transmitter and being configured to receive respective ones of the second modulated signal and the first amplified signal therefrom and generate a second amplified signal having a desired power level for transmission to the remote transponder;
a surface acoustic wave (SAW) filter connected to the second transmitter amplifier and being configured to receive the second amplified signal and remove unwanted harmonics therefrom and generate a transmitted signal in response thereto; and an RF transmitter antenna connected to the SAW filter and being configured to radiate the transmitted signal for receipt by a receiving antenna of the remote transponder.

9. A bio-sensor system powered by an electro-active polymer (EAP) generator and being adapted to provide a substantially stable voltage to a sensor assembly that is implantable in a patient such that physiological parameters thereof may be accurately measured, the bio-sensor system comprising:

a remote transponder configured to transmit a scanner signal to an implantable on-chip transponder and to receive a data signal therefrom;

the implantable on-chip transponder in wireless communication with the remote transponder and configured to receive the scanner signal and to transmit the data signal, the on-chip transponder including:

a sensor being configured to generate a sensor signal representative of the physiological parameter of the patient;

a power supply having the EAP generator adapted to be embedded in muscle tissue of the patient and being configured to generate a power signal for powering the on-chip transponder;

a radio frequency (RF) receiver configured to receive the power signal and the scanner signal and to filter, amplify and demodulate the scanner signal and generate a message signal for controlling the on-chip transponder;

an analog-to-digital (A/D) assembly connected to the power supply, the RF receiver and the sensor, the A/D assembly being configured to respectively receive the power signal, the sensor signal and the message signal and generate a digital signal in response thereto;

a data processor connected to the A/D assembly, the power supply and the RF receiver, the data processor being configured to respectively receive the power signal, the digital signal and the message signal and generate a data signal in response thereto; and an RF transmitter connected to the power supply, the data processor and the RF receiver and being configured to respectively receive the power signal, the data signal and the message signal and to modulate, amplify, filter and transit the data signal;

wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter;

wherein the EAP generator is configured to generate an alternating current (AC) voltage pulse during mechanical flexing of the EAP generator in response to movement of the muscle tissue within which the EAP generator is adapted to be embedded in, the power supply further including:

a pulse recovery circuit connected to the EAP generator and being configured to receive the AC voltage pulse therefrom and generate a generally coarse direct voltage signal in response thereto, the pulse recovery circuit including:

a rectifier being configured to receive the AC voltage pulse and allow positive current to pass through the pulse recovery circuit; and a storage device connected to the pulse recovery circuit and being configured to receive the direct voltage signal therefrom, the storage device being configured to store energy from cycles of the direct voltage signal for release as a substantially smooth DC voltage signal;

a controller connected to the storage device and configured to receive the direct voltage signal therefrom and generate a battery current;

a battery connected to the controller and being configured to be charged by the battery current and cooperating with the controller to generate a standby power signal and a DC voltage signal, the standby power signal being deliverable to the RF receiver;

a first regulator connected to the controller and being configured to receive the DC voltage signal therefrom and generate a first voltage signal to power the A/D assembly, the data processor and the RF transmitter;

a second regulator connected to the controller and being configured to receive the DC voltage signal therefrom and generate a second voltage signal to power the A/D assembly, the data processor and the RF transmitter; and a sensor reference supply connected to the controller and being configured to receive the DC voltage signal therefrom and generate a sensor reference voltage signal to power the sensor assembly.

10. The pulse recovery circuit of claim 9 further comprising a step-down voltage converter to reduce relatively high-levels of the AC voltage pulse to a level suitable for charging the battery.

11. The bio-sensor system of claim 9 wherein the storage device comprises a capacitor.

12. A bio-sensor system powered by an electro-active polymer (EAP) generator and being adapted to provide a substantially stable voltage to a sensor assembly that is implantable in a patient such that physiological parameters thereof may be accurately measured, the bio-sensor system comprising:

a remote transponder configured to transmit a scanner signal to an implantable on-chip transponder and to receive a data signal therefrom;

the implantable on-chip transponder in wireless communication with the remote transponder and configured to receive the scanner signal and to transmit the data signal, the on-chip transponder including:

a sensor being configured to generate a sensor signal representative of the physiological parameter of the patient;

a power supply having the EAP generator adapted to be embedded in muscle tissue of the patient and being configured to generate a power signal for powering the on-chip transponder;

a radio frequency (RF) receiver configured to receive the power signal and the scanner signal and to filter, amplify and demodulate the scanner signal and generate a message signal for controlling the on-chip transponder;

an analog-to-digital (A/D) assembly connected to the power supply, the RF receiver and the sensor, the A/D assembly being configured to respectively receive the power signal, the sensor signal and the message signal and generate a digital signal in response thereto;

a data processor connected to the A/D assembly, the power supply and the RF receiver, the data processor being configured to respectively receive the power signal, the digital signal and the message signal and generate a data signal in response thereto; and an RF transmitter connected to the power supply, the data processor and the RF receiver and being configured to respectively receive the power signal, the data signal and the message signal and to modulate, amplify, filter and transit the data signal;

wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter;

wherein the RF receiver is connected to the power supply and is configured to receive the standby power signal therefrom to allow the RF receiver to detect the scanner signal, the RF receiver including:

an RF receiver antenna configured to receive the scanner signal from the remote transponder;

a surface acoustic wave (SAW) filter connected to the RF receiver antenna and being configured to receive the scanner signal therefrom and filter the scanner signal of unwanted signals and generate a filtered scanner signal in response thereto;

a first RF amplifier connected to the SAW filter and being configured to receive the filtered scanner signal therefrom and generate a first amplified scanner signal in response thereto;

a SAW delay connected to the first RF amplifier and configured to receive the first amplified scanner signal therefrom and generate a compared signal;

a second RF amplifier connected to the SAW delay and being configured to receive the compared signal therefrom;

a pulse generator connected in parallel to the SAW delay at the first and second RF amplifiers and cooperating therewith to generate first and second pulse signals for receipt by respective ones of the first and second RF amplifiers such that the second RF amplifier generates a second amplified RF signal; and a detector-filter connected to the second RF amplifier and being configured to receive the second amplified RF signal therefrom and generate the message signal.

13. A bio-sensor system powered by an electro-active polymer (EAP) generator and being adapted to provide a substantially stable voltage to a sensor assembly that is implantable in a patient such that physiological parameters thereof may be accurately measured, the bio-sensor system comprising:

a remote transponder configured to transmit a scanner signal to an implantable on-chip transponder and to receive a data signal therefrom;

the implantable on-chip transponder in wireless communication with the remote transponder and configured to receive the scanner signal and to transmit the data signal, the on-chip transponder including;

a sensor being configured to generate a sensor signal representative of the physiological parameter of the patient;

a power supply having the EAP generator adapted to be embedded in muscle tissue of the patient and being configured to generate a power signal for powering the on-chip transponder;

a radio frequency (RF) receiver configured to receive the power signal and the scanner signal and to filter, amplify and demodulate the scanner signal and generate a message signal for controlling the on-chip transponder;

an analog-to-digital (A/D) assembly connected to the power supply, the RF receiver and the sensor, the A/D assembly being configured to respectively receive the power signal, the sensor signal and the message signal and generate a digital signal in response thereto;

a data processor connected to the A/D assembly, the power supply and the RF receiver, the data processor being configured to respectively receive the power signal, the digital signal and the message signal and generate a data signal in response thereto; and an RF transmitter connected to the power supply, the data processor and the RF receiver and being configured to respectively receive the power signal, the data signal and the message signal and to modulate, amplify, filter and transit the data signal;

wherein the power supply is configured to supply a substantially non-deviating sensor reference voltage to the sensor for accurate measurement of the physiological parameter, the remote transponder being configured to receive the data signal from the RF transmitter and to extract data representative of the physiological parameter;

wherein the remote transponder includes:

an oscillator configured to generate an analog signal at a predetermined frequency;

an encoder connected to the oscillator and configured to receive and modulate the analog signal and generate an encoded signal in response thereto;

a power transmitter connected to the encoder and configured to receive and amplify the encoded signal and generate the scanner signal; and a transmitting antenna connected to the power transmitter and configured to receive the scanner signal therefrom for radio transmission to the on-chip transponder.

14. The bio-sensor system of claim 13 wherein the remote transponder further includes:

a receiving antenna configured to receive the data signal from the RF transmitter;

a surface acoustic wave (SAW) filter connected to the receiving antenna and being configured to receive and filter the data signal of unwanted signals that may interfere with the remote transponder and generate a filtered data signal in response thereto;

a first RF amplifier connected to the SAW filter and being configured to receive the filtered data signal therefrom and generate a first amplified data signal in response thereto;

a SAW delay connected to the first RF amplifier and configured to receive the first amplified data signal therefrom and generate a compared signal;

a second RF amplifier connected to the SAW delay and being configured to receive the compared signal therefrom;

a pulse generator connected in parallel to the SAW delay at the first and second RF amplifiers and cooperating therewith to generate first and second pulse signals for receipt by respective ones of the first and second RF amplifiers such that the second RF amplifier generates a second amplified RF signal; and a detector-filter connected to the second RF amplifier and being configured to receive the second amplified RF signal for extraction of digitized data therefrom.

15. The bio-sensor system of claim 14 further including a decoder connected to the detector-filter and being configured to receive the second amplified RF signal for extraction of digitized data therefrom.

16. The bio-sensor system of claim 15 further including:
a plurality of sensors, each one of the sensors being operative to sense a distinct physiological parameter of the patient and generate a sensor signal representative thereof;
wherein the decoder is configured to select one or more of the plurality of the sensors from which to receive data.

17. A method of remotely monitoring physiological parameters using a bio-sensor system comprising a remote transponder and an on-chip transponder having a sensor implantable in a patient, the on-chip transponder being powered by a power supply including an electro-active polymer (EAP) generator embedded in muscle tissue of the patient, the method comprising the steps of:
a. remotely generating and wirelessly transmitting a scanner signal from the remote transponder, the scanner signal containing a telemetry data request;
b. receiving the scanner signal at the on-chip transponder and filtering, amplifying and demodulating the scanner signal to generate a message signal in response thereto;
c. generating a power signal in response to mechanical flexing of the EAP generator due to movement of the muscle tissue within which the EAP generator is embedded;
d. receiving the power signal at the sensor and sensing at least one physiological parameter of the patient and generating an analog sensor signal in response thereto;
e. receiving the power signal, the analog sensor signal and the message signal at an analog-to-digital (A/D) assembly and generating a digital signal representative of the analog sensor signal;
f. receiving the power signal, the message signal and the digital signal at a data processor and preparing the digital signal for modulation and generating a data signal representative of the digital signal;
g. receiving the power signal, the message signal and the data signal at radio frequency (RF) transmitter and modulating, amplifying, filtering and wirelessly transmitting the data signal; and
h. receiving the data signal at the remote transponder and extracting data representative of the physiological parameter of the patient.

18. The method of claim 17 wherein the method of generating the power signal comprises the steps:
generating an alternating current (AC) voltage pulse at the EAP generator during mechanical flexing thereof;
receiving the AC voltage pulse at a pulse recovery circuit and generating a generally coarse direct voltage signal in response thereto;
storing energy from cycles of the direct voltage signal at a storage device for release as a substantially smooth DC voltage signal;
receiving the DC voltage signal at a controller and generating a battery current in response thereto;
providing the battery current to a battery for charging thereof;
releasing current back to the controller and generating a DC voltage signal in response thereto;
receiving the DC voltage signal at a first regulator and generating a first voltage signal in response thereto;
receiving the DC voltage signal at a second regulator and generating a second voltage signal in response thereto;
combining the first and second voltage signals to generate the power signal for powering the A/D assembly, the data processor and the RF transmitter; and
receiving the DC voltage signal at a sensor reference supply and generating a sensor reference voltage for powering the sensor assembly.

19. The method of claim 18 wherein the sensor is a 2-pin glucose sensor having an electrode assembly with first and second terminals adapted to be in fluid communication with the patient's blood for sensing a glucose level of the patient, step (d) further comprising the steps of:
tuning the power signal with a first precision resistor to generate a sensor reference voltage of about positive 0.7 volts for excitation of the glucose sensor;
receiving the sensor reference voltage at a first operational amplifier and generating a precision sensor reference voltage;
monitoring the precision sensor reference voltage with a voltmeter connected to the first operational amplifier and the first precision resistor to establish a sensor operating point;
buffering the precision sensor reference voltage with the first operational amplifier in cooperation with the voltmeter to generate a substantially accurate sensor reference voltage;
applying the substantially accurate sensor reference voltage to the first terminal to cause current to discharge from the second terminal in response to a reaction with the patient's blood at the first and second terminals;
receiving the discharging current at a second operational amplifier, the current being proportional to the glucose level of the patient's blood; and
tuning a second precision resistor connected to the second operational amplifier to form a voltage divider with the glucose sensor;
measuring the discharging current with the second precision resistor in cooperation with the second operational amplifier; and
generating the sensor signal that is substantially proportional to the glucose level.

20. The method of claim 19 wherein the sensor is a 3-pin glucose sensor additionally including a third terminal co-located with the first and second terminals and adapted to be in fluid communication with the patient's blood, step (d) further comprising the steps of:
diverting a portion of the current away from the second terminal by discharging current at the third terminal during application of the substantially accurate sensor reference voltage to the first terminal;
receiving the discharging current at an auxiliary control circuit connected between the third electrode and the second operational amplifier; and
monitoring and controlling an amount of current discharging from the third terminal in order to stabilize the substantially accurate sensor reference voltage applied to the first terminal and increase the operational life of the glucose sensor.

* * * * *